United States Patent
Hendricks et al.

[11] Patent Number: 5,989,852
[45] Date of Patent: *Nov. 23, 1999

[54] INDICATOR SYSTEMS FOR DETERMINATION OF STERILIZATION

[75] Inventors: Judy K. Hendricks, Albuquerque, N.Mex.; Shaundrea L Rechsteiner, Lambertville, Mich.; Joel R. Gorski, Marrietta, Ga.

[73] Assignee: North American Science Associates, Northwood, Ohio

[ * ] Notice: This patent is subject to a terminal disclaimer.

[21] Appl. No.: 09/184,352

[22] Filed: Nov. 2, 1998

Related U.S. Application Data

[63] Continuation of application No. 08/735,992, Oct. 24, 1996, Pat. No. 5,830,683
[60] Provisional application No. 60/010,312, Jan. 22, 1996, and provisional application No. 60/025,514, Sep. 5, 1996.
[51] Int. Cl.$^6$ ............... C12Q 1/22; C12Q 1/54; C12Q 1/32; C12Q 1/02
[52] U.S. Cl. ................ 435/31; 435/14; 435/26; 435/29; 435/287; 435/807; 435/810; 422/50
[58] Field of Search ................. 435/31, 14, 26, 435/29, 287, 807, 810; 422/50

[56] References Cited

U.S. PATENT DOCUMENTS

| Re. 34,515 | 1/1994 | Foley | 435/31 |
|---|---|---|---|
| 2,984,172 | 5/1961 | Roberts et al. | 435/31 |
| 3,078,628 | 2/1963 | Ready | 435/31 |
| 3,450,036 | 6/1969 | Broesma | 435/31 |
| 3,694,992 | 10/1972 | Hunt | 435/31 |
| 3,811,242 | 5/1974 | Hayford, Jr. et al. | 435/31 |

(List continued on next page.)

FOREIGN PATENT DOCUMENTS

| 3335754 | 8/1983 | Germany . |
|---|---|---|
| 2084954 | 4/1982 | United Kingdom . |
| 2113389 | 8/1983 | United Kingdom . |
| 2186974 | 8/1987 | United Kingdom . |
| 9532742 | 12/1995 | WIPO . |

*Primary Examiner*—Louise N. Leary
*Attorney, Agent, or Firm*—Baker & Botts, LLC

[57] ABSTRACT

This invention relates to novel apparatus and methods for inserting and positioning a compressible material into a container and for using the container for detecting a specific environmental parameter or combination of parameters, or for determining the effectiveness of a sterilization procedure. Precise positioning of a plug of compressible material in a container has been discovered to provide flexibility necessary for production of indicator systems that vary in their response to sterilizing conditions to reflect the efficacy of sterilizers based on different modes of sterilization and reproduceability necessary for accurate monitoring of each mode. The invention also relates to test indicators containing controlled volumes of compressed, gas-permeable materials and to methods for using test indicators for determining the efficacy of different types of sterilization processes. The test indicator consists of a plurality of interactive enzymes in a container with at least one opening. The opening is filled with a compressed cylindrical foam insert and the test indicator is placed into the sterilization chamber. The foam insert regulates the amount of sterilant such as steam, gas, chemicals or plasma entering the test indicator. After the sterilization cycle is complete, the foam insert is removed and the remaining components of the enzyme system are combined. If the proper sterilization conditions were not met, the interactive enzyme system remains active, and a color product forms upon the addition of the remaining components of the enzyme system. If the proper sterilization conditions were met, the sterilant destroys the interactive enzymes and no color product is formed. Inactivation of the enzyme system parallels the inactivation of bacterial spores subjected to the sterilization process. Results are available in from a few seconds to a few hours. The test indicator can also be placed into a container with material such that the designs simulates an environmental parameter test of the sterilization process.

26 Claims, 10 Drawing Sheets

U.S. PATENT DOCUMENTS

| | | | |
|---|---|---|---|
| 3,942,467 | 3/1976 | Witonsky | 435/31 |
| 4,121,399 | 10/1978 | Verville | 435/31 |
| 4,457,125 | 7/1984 | Fishburne | 435/31 |
| 4,525,316 | 6/1985 | Galla et al. | 435/31 |
| 4,576,795 | 3/1986 | Bruso | 435/31 |
| 4,579,715 | 4/1986 | Bruso | 435/31 |
| 4,594,834 | 6/1986 | Schmidt et al. | 435/31 |
| 4,602,472 | 7/1986 | Ampolini et al. | 435/31 |
| 4,636,472 | 1/1987 | Bruso | 435/31 |
| 4,692,307 | 9/1987 | Bruso | 435/31 |
| 4,699,765 | 10/1987 | Hambleton | 435/31 |
| 4,839,291 | 6/1989 | Welsh et al. | 435/31 |
| 4,848,222 | 7/1989 | Fleissner | 435/31 |
| 4,902,478 | 2/1990 | Hambleton | 435/31 |
| 5,046,304 | 9/1991 | Alameda et al. | 435/31 |
| 5,056,371 | 10/1991 | Graudejus et al. | 435/31 |
| 5,073,488 | 12/1991 | Matner et al. | 435/31 |
| 5,085,802 | 2/1992 | Jalinski | 435/31 |
| 5,182,212 | 1/1993 | Jalinski | 435/31 |
| 5,200,147 | 4/1993 | Augurt | 435/31 |
| 5,223,401 | 6/1993 | Foltz et al. | 435/31 |
| 5,252,484 | 10/1993 | Matner et al. | 435/31 |
| 5,366,872 | 11/1994 | Hird et al. | 435/31 |
| 5,378,430 | 1/1995 | Nieves et al. | 435/31 |
| 5,401,156 | 3/1995 | Anderson | 435/31 |
| 5,418,167 | 5/1995 | Matner et al. | 435/31 |
| 5,435,971 | 7/1995 | Dyckman | 435/31 |
| 5,486,459 | 1/1996 | Burnham et al. | 435/31 |
| 5,830,683 | 11/1998 | Hendricks et al. | 435/31 |

COMPONENTS

COMPLETED SYSTEM

INCUBATE FOR SPECIFIED TIME

FIG. 8B1
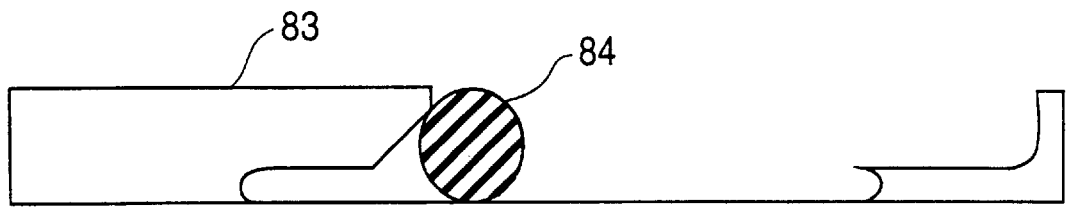
FIG. 8B2
FIG. 8B3
FIG. 8B4
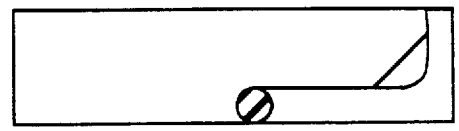

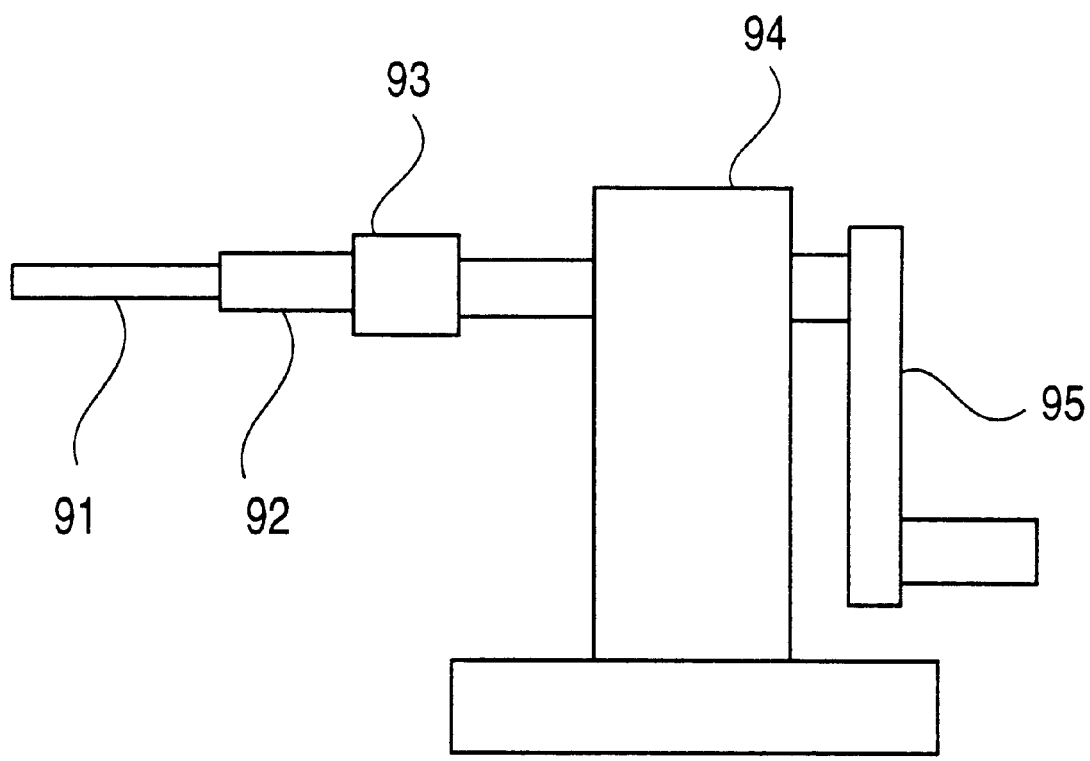

INDICATOR SYSTEMS FOR DETERMINATION OF STERILIZATION

This application is a continuation of application Ser. No. 08/735,992, filed Oct. 26, 1996 entitled INDICATOR SYSTEMS FOR DETERMINATION OF STERILIZATION.

This application claims benefit of Provisional Appl. 60/010,312 filed Jan. 22, 1996 and Provisional Appl. 60/025,574 filed Sep. 5, 1996.

BACKGROUND OF THE INVENTION

1. Field of the Invention

This invention relates to indicator systems comprising a container containing an environmental sensing system and compressible material separating the sensing system from its surroundings. Indicator systems can be used for the determination of sterilization in a variety of sterilizations processes or in determining the efficacy of an environmental test such as a test for air removal from a sterilization chamber.

2. Description of the Background

In health care, as well as many other industries, it is nearly always necessary to monitor the effectiveness of processes used to sterilize equipment such as medical devices, instruments and other disposable or nondisposable articles, and often waste. In these settings, sterilization is generally defined as the process of completely destroying all viable microorganisms including structures such as viruses, spores, yeasts and fungus. Standard practice in hospitals is to include a sterility indicator in a batch of articles to be sterilized. The use of sterility indicators allows a direct and sensitive approach to assay the lethality of the sterilization process.

A standard type of biological sterility indicator includes a known quantity of test microbial spores. This indicator is placed into the sterilization chamber and exposed to the sterilization process along with the objects to be sterilized. The test microorganisms, for example *Bacillus stearothermophilus* or *B. subtilis* spores, are incubated for a specified period of time under conditions which favor proliferation and examined for possible growth, such as turbidity in the growth medium or the presence or absence of certain metabolic products of any surviving microorganisms. Positive growth, indicating the presence of a viable spore, indicates that the sterilization process was insufficient to destroy all of the microorganisms. While the apparatus for containing the spores has varied continuously, the general sterility detection process has not. Many such indicators are disclosed in U.S. Pat. Nos. 3,239,429; 3,440,144; 4,596,773; 4,717,661; 4,732,850 and 5,167,923.

The largest use of sterility indicators occurs in research and the health care industry. Typically, such facilities have limited resources and must reuse their materials and instruments within 24 to 48 hours after sterilization and often immediately. Conventional sterility indicators normally require that the microorganisms be cultured for at least two and often up to seven days to assure adequate detection of any surviving microorganisms. During this time, items which go through the sterilization process, should not be used until the results of the spore viability test have been determined. Consequently, a holding period for sterility verification is often required. This holding period is both impractical and inefficient and, thus, the major drawback of all conventional sterility indicators.

The use of an enzyme and its subsequent activity as an indicator in detecting sterility has been described in U.S. Pat. No. 5,073,488. This technology has been greatly advanced with U.S. Pat. No. 5,486,459 which describes the use of a plurality of interactive enzymes. This technique involves subjecting a set of interactive enzymes to a sterilization cycle. Following completion of the cycle, the set is incubated with a substrate which is acted upon by the enzymes and transformed into a detectable product. Enzyme-modified product can be detected, for example, calorimetrically or fluorometrically. This method has been proven to be accurate and detection speeds are greatly accelerated as compared to spore systems. In fact, definitive results using interactive enzyme technology can be determined in less than a few minutes.

Sterility indicators are often placed in special packaging or wraps to simulate the condition of wrapped goods being processed in a sterilizer. If the articles to be sterilized are in special wrappings or packaging, the sterilant needs to effectively pass through the wrappings to destroy microorganisms on the article. To test the effectiveness of the sterilant passing through additional materials, sterility indicators are placed in challenge packs. These packs impede the sterilant as would the wrappings and thereby represent the conditions of wrapped goods in a sterilizer.

There are international standards such as the International Organization for Standardization (ISO) and the European Standards (EN) that deal with sterilization testing including steam sterilization. International standards dealing with biological indicators and testing procedures are found in the ISO 11138 series and EN 860 series. International standards for the air removal tests for pre-vacuum steam sterilizers comprises a chemical indicator in a test pack are found in the ISO 11140 series and EN 867 series. These packs incorporate the Bowie-Dick test and have similar performance standards as seen in AAMI (American Association of Medical Instrumentation), but use different testing procedures.

AAMI has proposed guidelines for challenge packs containing indicators that are assembled by hospital workers to simulate the conditions of wrapped goods in a steam or ethylene oxide sterilizer. Materials required for an AAMI challenge pack for a steam sterilizer include sixteen freshly laundered huck towels, autoclave tape and sterility indicators. In one method, each towel is folded length-wise into thirds and then folded width-wise in half. Towels are placed one on top of another with the folds opposite each other. Sterility indicators are placed between the eighth and ninth towels and the pack is secured with autoclave tape. The AAMI steam challenge pack is placed into a steam autoclave for the appropriate amount of time. Upon completion of a cycle, the indicators are processed to determine if the sterilization process was sufficient to inactivate the indicators buried in the pack.

In the case of ethylene oxide sterilization, AAMI recommends placing a sterility indicator into a plastic syringe so that the plunger is not touching the indicator. In this case, the needle end of the syringe is open. Two such syringes are placed in the center of a stack of folded towels and the stack is wrapped in a single towel. For routine monitoring, the syringe and indicator can be wrapped in a single towel and placed into a peel pouch.

Tests are also performed that evaluate the effectiveness of air removal in a prevacuum steam sterilizer. Prevacuum steam sterilizers are used to minimize the amount of air present in the sterilization chamber, thus enhancing the penetration of steam into porous loads. A prevacuum sterilizer air removal test is also known as the Bowie-Dick test or a prevacuum sterilizer residual air test.

AAMI guidelines for the Bowie-Dick test pack state that the standard pack is made using folded cotton surgical towels. Several towels are folded to create a stack 10 to 11 inches high with a rectangular border of 9 by 12 inches. A Bowie-Dick test sheet, which comprises a pattern of chemical indicator ink or indicator type on a porous sheet, is placed in the center of the pack. The pack is wrapped in a single cotton wrap and processed in a steam prevacuum sterilizer. The acceptance criterion is that the test sheet or tape darkens uniformly after processing. In other words, the chemical indicator ink changes color upon exposure to steam and if the entire sheet shows a uniform color change, there was no residual air to impede the steam.

AAMI guidelines state that other devices may be used in place of the AAMI challenge packs and Bowie-Dick tests if they provide equivalent results to the AAMI packs. Enclosure of sterilization indicators in various fibrous materials, analogous to textiles such as the towels used in the AAMI challenge packs, has been proposed in U.S. Pat. Nos. 5,200,147, 5,252,484 and 5,223,401. Packages in which a sterilization indicator is surrounded by porous material to replace some of the towels are described in U.S. Pat. No. 4,692,307.

Compressible material, such as foam, has a wide variety of uses when placed inside a container. For example, compressible material in a container could be used for absorbing shock vibrations or sound, as a barrier for solids, liquid or gases, for separating components, for absorbing liquids and/or for application of liquids such as ink, paint or antiseptics. A major drawback of using compressed material in a container is the expense of compressing the material into the container. The conventional process for inserting compressed material into a container was for the material to be compressed by hand and forced manually into the container. This method is slow, often unreproducible and, consequently, expensive.

U.S. Pat. No. 3,811,242 relates to an apparatus for compressing blocks of compressible material, particularly polyurethane, to a small percentage of their original volume by compressing in the direction of the longest axis of the block, successively, and in perpendicular directions until the block is of the desired size. Restraining bands are applied to the block to prevent rebound or expansion in all directions of compression.

U.S. Pat. No. 5,400,067 relates to an apparatus for inserting a rectangular foam insert into the rectangular ink chamber of an ink jet print head. The apparatus involves two flat pistons opposing two fixed plates which form a right angle. Pressure is exerted by each of the two pistons successively against two adjacent sides of the foam rectangle to compress the foam to a cross-sectional area smaller than the area inside the ink chamber. The ink chamber is positioned over a rectangular walled tube formed by extensions of the pistons and the opposing plates, and then a ram moving orthogonally to the two pistons pushes the foam into the ink chamber. This device requires successive compression in perpendicular directions by three moveable components.

U.K. Patent number 2,084,954 relates to a method for packaging a cylindrical sponge into a tube. The sponge is placed on a support plate between two jaws having concave arcuate section. According to this method, one jaw is fixed and a second jaw moves across the plate. Sponge is first compressed by a platen parallel to the support plate which descends toward the support plate until the separation between the platen and the support plate is equal to the desired diameter of the compressed sponge. Sponge is further compressed by movement of the moveable jaw across the plate until the two jaws abut, forming a cylindrical cavity containing the compressed sponge. The tube is axially aligned with the cavity and the sponge is pushed from the cavity into the tube by a plunger. This device requires successive compression in perpendicular directions by numerous moveable components that must be kept in perfect alignment.

U.S. Pat. No. 4,602,472 relates to a device for packaging rolls of fiber insulation by compressing them in a compression chamber which employs double stage compression. A pivoting stage compresses the roll in a first direction, analogous to the platen of U.K. Patent number 2,084,954. A ram having a concave semicylindrical surface compresses the roll in a second direction to form a cylinder of the desired size. Subsequently, a discharge ram pushes the roll along the axis of the cylinder into a tubular member suitably sized to receive the roll. A paper or plastic sleeve having a closed end is placed over the tubular member, and the roll pushed through the tubular member into the sleeve, thereby pulling the sleeve off the tubular member and enclosing the roll in the sleeve material.

U.S. Pat. No. 5,208,954 relates to a device for inserting, into cavities in masonry building blocks, preformed insulating foam inserts wherein the foam inserts are slightly larger than the cavities. In the device, the foam is positioned over a channel which in turn is aligned with the cavity in the block, the channel having a throat with curved sidewalls. A tamping head pushes the foam insert through the channel where the foam is compressed by the throat to have a cross-section small enough to fit into the cavity.

U.S. Pat. No. 3,450,036 relates to a device for packing loose granular material such as potting soil around a plant and depositing the packing material and plant into container, such as a pot or bag. The device includes at least two arcuate sections that fit together to form a cylinder holding the plant and soil. A ram pushes the plant and soil together out of the cylinder and into the container. As potting soil is not compressible to any significant degree, the device is a forming apparatus, but not a compressing apparatus.

None of these apparatus and methods are satisfactory for reproducibly inserting and positioning a compressible material such as foam or sponge into a vial.

SUMMARY OF THE INVENTION

The present invention overcomes the problems and disadvantages associated with current strategies and designs and provides novel methods and apparatus for inserting and positioning a compressible material into a container and novel methods and test indicators for determining the effectiveness of a sterilization procedure or measuring a parameter of the sterilization process.

One embodiment of the invention is directed to apparatus for consistently positioning a compressible material in a container. Precise positioning of a plug of compressible material in a container has been discovered to provide the flexibility necessary for production of indicator systems that vary in their response to sterilizing conditions to reflect the efficacy of sterilizers based on different modes of sterilization and the reproduceability necessary for accurate monitoring of each mode.

Another embodiment of the invention is directed to methods for reproducibly compressing a gas-permeable, compressible material and positionally inserting the compressed material into a container. The apparatus is particularly useful for manufacture of adjustable indicator systems for the determination of the effectiveness of sterilization processes using steam, gas, chemical and plasma sterilizers. These systems can be used for many types of tests in hospitals, laboratories and clinics, as well as in research institutions, in food and environmental technology and in technologies that utilize sterilization in manufacturing, production or waste disposal.

Another embodiment of the invention is directed to test indicators containing a biological material separated from the sterilizer environment by a controlled volume of compressed, gas-permeable material. The material controls access of the sterilizing medium to the biological material. Volume, size, shape or density of compressed, gas-permeable material in the indicator is determined by the particular sterilization process.

Another embodiment of the invention is directed to a test indicator for determining the effectiveness of a sterilization procedure. Test indicators comprise an outer container having liquid impermeable and substantially gas non-absorptive walls, at least one opening leading into a chamber which contains one or more components of an interactive enzyme system, and a liquid impermeable or liquid semi-permeable gas-transmissive barrier between the components and the opening. These components may be fixed to a solid support or free-floating in a non-aqueous or partially-aqueous solution. After sterilization, the user simply mixes the components in the container with the remaining components of the enzyme system. If any enzyme activity is present, the enzymes plus any necessary coenzymes, cofactors and catalysts will interact with the substrate forming detectable product which can be assayed to determine the effectiveness of the sterilization procedure.

Another embodiment of the invention is directed to methods for determining the efficacy of different types of sterilization processes. The test indicator consists of a plurality of interactive enzymes in a container with at least one opening. The opening is filled with a compressed cylindrical foam insert. The test indicator is placed into the sterilization chamber. The foam insert regulates the amount of sterilant such as steam, gas, chemicals or plasma entering the test indicator to achieve a response that can be equivalent to indicators containing bacterial spores. After the sterilization cycle is complete, the foam insert is removed and the remaining components of the enzyme system are combined. If the proper sterilization conditions were not met, the interactive enzyme system remains active, and a color product forms upon the addition of the remaining components of the enzyme system. If the proper sterilization conditions were met, the sterilant has destroyed components of the interactive enzyme system and no color product is formed. Inactivation of the enzyme system parallels the inactivation of bacterial spores subjected to the sterilization process. Results are available in from a few seconds to a few hours.

Another embodiment of the invention is directed to methods for adjusting the sensitivity of sterility indicators of the invention to one or more predetermined environmental parameters. Test indicators, substantially identical to the sterility indicators, are exposed to a sterilization procedure and the effectiveness of that procedure determined. The position and/or composition of the gas-transmissive plug of another test indicator is adjusted and the another test indicator is exposed to the sterilization process. From the effectiveness of each test indicator for reacting to the environmental parameter, the sensitivity of the sterility indicator can be accurately and quantitatively adjusted.

Another embodiment of the invention is directed to methods for creating a challenging environment for the penetration of sterilant. Using an enzyme, spore or chemical indicator in a container with a controlled volume of gas-permeable material for creating a reproducible resistance for the sterilant penetration, a test pack for evaluating sterilant penetration or air removal is created.

Other embodiments and advantages of the invention are set forth, in part, in the description which follows and, in part, will be obvious from this description or may be learned from the practice of the invention.

DESCRIPTION OF THE DRAWINGS

FIG. 9 A front view of an apparatus with a rotating container held by a flexible tube used for insertion of compressible materials.

DESCRIPTION OF THE INVENTION

Figure 1A:
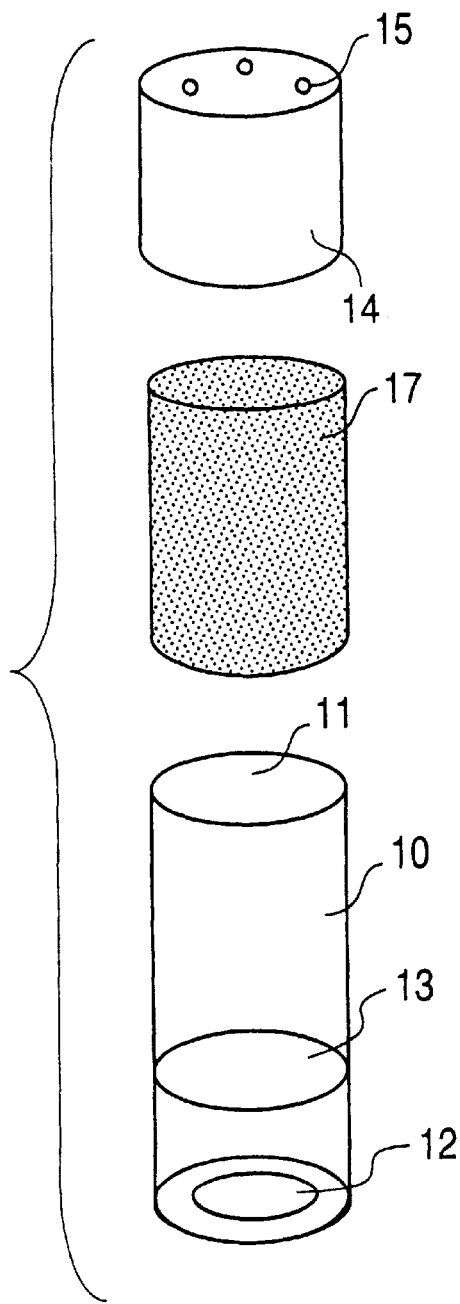
FIG. 1 Diagram of the construction of a container for a rapid sterility indicator.

As embodied and broadly described herein, the present invention is directed to methods and apparatus for inserting and positioning a compressible material into a container, to test indicators containing controlled volumes of compressed, gas-permeable material for determining the effectiveness of a sterilization procedure and to methods for using the test indicators.

Conventional sterility indicators typically comprise viable spores which are exposed, along with the objects to be sterilized, to a sterilizing condition. After exposure, the indicator is removed and the spores cultured under defined conditions. Culturing takes days to a week for any sort of definitive results. Indicators often require post-sterilization incubation at higher than ambient temperatures to provide detectable results.

It had been discovered that indicators comprising enzymes and preferably interactive enzyme systems are a suitable substitute for spores. Inactivation of an enzyme system by a sterilization process mimics the death of viable spores. It has also been discovered that an insert design comprised of a compressible material such as foam provides accurate as well as reproducible results with these sterility indicators.

Indicators comprising multiple interacting enzymes and adjustable foam inserts overcome the problems and disadvantages present with current strategies and designs for evaluating sterilization processes and can provide nearly instantaneous and reproducible results. The indicator system is simple to use and requires minimal training. Reliable results are achieved without specialized instructions or equipment. Surprisingly, indicators are also useful for monitoring many types of sterilization processes. The amount and/or length of the insert is simply adjusted during manufacture according to the requirements of the process. In all cases, the results that can be achieved are rapid as well as reliable and reproducible.

One embodiment of the invention is directed to a test indicator device (the rapid sterility indicator or RSI) for the rapid determination of the efficacy of different types of sterilization processes (e.g., steam heat, dry heat, chemical sterilant, plasma). Indicators comprise a compressible material placed as a plug into an opening or sleeve of a container wherein the container or sleeve has a smaller cross-sectional area than the cross-section of the article when not compressed. The container is made of non-adsorptive material such that the only pathway for the sterilant is through the foam insert. That foam insert regulates the amount of sterilant (e.g., steam, gas, chemicals or plasma) entering the test indicator and the amount of foam utilized may be regulated according to the sterilizing process. Indicator reagents are placed in the container with at least one opening and the opening is filled with the compressed cylindrical insert.

The container may be a vial in which a foam stopper is to be inserted or a cylindrical tube in which the plug is partially permeable to liquid. This foam stopper forms a filter for fluids passing through the tube. The compressible material is a gas-permeable, open-celled natural or artificial (plastic) foam or sponge which may be comprised of, for example, polyurethane, polyester, polyether, cellulose, melamine or a combination of these materials. Foam density, pore size, cell structure (the percent of opened cells), size, shape, amount of foam, stiffness and tensile strength can be chosen to fit the particular situation.

For a container with a cross-sectional area of from about 0.03 to about 0.2 square inches, the compressed material has a non-compressed cross-sectional area of from about 0.2 to about 3.5 square inches. The inside portion of the plug is from about 0.4 to about 2.0 inches in length, preferably about 1.2 to 1.5 inches, with an overhang portion. Preferably, the overhang portion is less than about 0.5 inches in length. These areas and lengths can be adjusted accordingly for larger and smaller sized containers. The inside length and/or the length of the overhang portion can be adjusted very easily during manufacture. Optimal lengths can be determined empirically by one of ordinary skill in the art according to the parameters of a particular sterilization process. Shorter lengths tend to be most useful for chemical process whereas longer plug and overhang lengths are typical for steam sterilization. Adjustments can also be made to the distance of the plug from the sensing system and the density, the degree of compactness and the composition of the plug. All of these factors affect the sensitivity of the indicator to the sterilization process.

As indicators are easily adjusted, another advantage is that indicators can be modified to meet all major as well as minor alterations of a sterilization process. It is not necessary to switch to another type of sterilization indicator upon changing sterilization processes or sterilants. The insert can be varied to optimize the sterility indicator and thereby meet multiple situations and different sterilants as well as different sterilization protocols. It is also not necessary to change the type of sterility indicator upon changing the sterilization process. As an adjustment can be as simple as changing the length of the plug, it is a very straight forward matter to implement a change during manufacture with little to no added expense.

Sterility indicators further contain spores, enzymes, an enzyme system or combinations thereof, as sensing reagents that provide an indication of sterility. These reagents may be a liquid or solid. Liquids are preferably in a non-aqueous or partially aqueous medium. Solids may be membranes such as disks and are preferably powders or tablets that contain granularized reagents. Such reagents can be made into a granulation by fluid-bed granulation. Fluid-bed granulation takes different components and coimmobilizes these components into clusters. Clusters comprise different components dried onto a seed particle. The granulation process begins by suspending a seed material in air and spraying a liquid material onto the seed. Other components are added either to the liquid solution or to the fluidized particles. Particles adhere to the liquid and form clusters of different components and, finally, moisture is removed from the clusters. The granulation process can be used to manufacture enzymes coimmobilized in a granulation or pressed into a tablet with little moisture as enzymes are typically most stable when packaged without water.

Granulation begins with a dry powder, referred to as the seed, which functions as a solid support. Seed material can be an inert substance or one of the components of the granulation and is placed into the process chamber. Controlled airflow into the chamber creates an air suspension of the particles and, thus, particles are suspended or fluidized. Once the particles are suspended in the air, a liquid solution is sprayed onto the solid particles.

The humidity, temperature and air velocity are controlled in the chamber. Humidity is kept very low and the temperature is increased to approximately 35° C. The liquid, after being sprayed onto the seeds, evaporates and a granulation is formed. Seeds are coated with the different ingredients forming the clusters and water is removed.

There are several ways two enzymes can be formed into a granulation product. For example, each enzyme can begin as a liquid solution. Using an inert solid seed material such as cellulose, one enzyme is sprayed onto the fluidized cellulose seeds. A second granulation is made of the second enzyme and the two granulations are blended together. Alternatively, the two enzymes could be mixed together as one liquid solution and sprayed onto the seed material. Alternatively, one or both enzymes could begin as a solid material. The solid material would be used as the seed material and a liquid binder solution is sprayed onto the seeds. Liquid solution is needed to create granulation and the solid, dry components adhere to the liquid solution. While the material is being fluidized, the high temperature and low humidity remove water from the granulation product and the enzymes are coimmobilized onto the seed material.

Granulations can also be pressed into tablets. For example, several granulations can be blended together using mechanical blenders and pressed into a single tablet. When working with several granulations, each can be tested for activity and then the final composition of the tablets activity can be adjusted by altering the amounts of each granulation component. The final enzyme tablet will contain very little water, typically less than about 5% and preferably less than about 3%.

Indicator reagents suitable for some applications comprise a single enzyme, such as that described in U.S. Pat. No. 5,073,488, along with the substrates, reagents, catalysts, cofactors, etc., necessary to produce a detectable product. Indicator reagents may also comprise multiple components of an interactive enzyme system. The enzyme system preferably comprises a known mix of enzymes, coenzymes, catalysts, cofactors, substrates, other reaction reagents or combinations such as those provided in U.S. Pat. No.

5,486,459. Enzyme systems comprise a plurality of enzymes that rapidly catalyze a series of coupled reactions which together produce a detectable product.

Another embodiment of the invention is directed to a method for determining the effectiveness of a sterilization process. The basic process comprises subjecting at least one and preferably multiple components of an enzyme system to a sterilization procedure. The enzyme system comprises a known mix of enzymes, coenzymes, catalysts, cofactors, substrates, other reaction reagents or combinations thereof, which is housed in a test indicator. The components have an interdependent activity which correlates with the viability of the microorganisms used in state-of-the-art biological indicators.

According to this method, a test indicator is placed into the sterilization chamber and subjected to a sterilization process. After the sterilization cycle is complete, the foam insert may be removed and the remaining components of the enzyme system added to form a mixture. The mixture is incubated, if necessary, for a period of time sufficient to allow for product formation from the interaction of the enzymes with the substrate. Incubation times range from a few seconds to a minute and are preferably less than about 15 minutes, more preferably less than about 10 minutes and even more preferably less than about 3 minutes. If desirable, incubation can be eliminated and the product detected almost immediately or in less than about 20 seconds. A detectable product will form if all of the components of the enzyme system, including the plurality of enzymes, are present and active. A positive result is observed when each exposed component survives denaturation and is able to function interactively to produce a detectable enzyme-modified product. The enzyme-modified product as an indicator of residual activity is visually detectable within 1 to 60 minutes and preferably within seconds. Any change detected, which is preferably a color change, is an indication to an observer that the sterilization cycle had not inactivated certain components and, thus, was insufficient to assure sterilization of other articles exposed to the sterilization procedure. Conversely, an absence of a color change indicates that the sterilization procedure had inactivated at least one of the components thereby preventing the interactive reaction from taking place and thus, an equivalent of rapidly and directly detecting the survivability of bacterial spores in a similar conventional test.

Lack of detectable enzyme-modified product within the established period of time indicates a sterilization cycle which has been lethal to the function of the interactive enzyme system as well as lethal to a viable $10^6$ population of *Bacillus stearothermophilus* spores. Generally, these values are expressed as D-values, which is the time taken at a given temperature to reduce the viable population of test microorganisms to ten percent of its original value. Inactivation of the enzyme system parallels the inactivation of bacterial spores subjected to the sterilization process, except that the result may be available in minutes or seconds as compared to at least overnight incubation required for detection of bacterial growth from spores.

Product can be detected using a variety of procedures. For example, substrate can be labeled and the resulting radioactivity or enzymatic, electrical or fluorometric activity of the product detected using conventional devices such as, for example, those utilized for determining the effectiveness of sterilization procedures. Preferably, product is detected visually as visual detection is simple and inexpensive requiring little training and no specialized instrumentation outside of what would be found in a typical working environment.

The relationship between the components is very relevant to a determination of sterility because it is not simply a chemical or enzyme reaction, but an enzyme interaction reflective of the presumptive physiological state of microorganisms within the chamber. The ability of the methods of the invention to rapidly determine the efficacy of a sterilization cycle is based upon the discovery that the survival of functional capability of an enzyme system is necessary for the production of an enzyme-modified product. The rapidity of formation of the enzyme-modified product from the interacting enzymes is due, at least in part, to coimmobilization wherein the close proximity of two or more components of the enzyme system on a common solid support such that diffusion controlled exchange with bulk solution is limited. This process is further supplemented by component channeling or, the bringing together of two or more components of sequential reactions at a surface or microenvironment to further limit diffusion-controlled exchange with bulk solution. Component channeling with regard to enzymes is described in I. Gibbons et al. (Meth. Enzymol. 136:93–103, 1987).

The ability of the components of an enzyme system to survive conditions which only partially kill test microorganisms is dependent, at least in part, upon the use of a semi-permeable barrier between the sterilant and the enzymes, and that the interactive enzyme system will remain active following a sterilization cycle which is insufficient to kill the test microorganisms. It is not necessary that the barrier be impermeable to microorganisms such as bacteria, only that it be fluid permeable to permit exposure of the indicator components to the sterilizing environment. Such as through open cells of a compressible material or around the sides of a closed cell compressible material. This provides a direct correlation of spore viability with the interactive activity of the enzymes of the system which, following an inadequate sterilization cycle, is sufficient to convert a substrate system for those enzymes to a visually detectable concentration of product within a relatively short time, preferably 1 to 60 minutes. The basis for the correlation between the activity of the enzymes and other components to the germination and growth of microorganisms is due to the commonality of both in their reliance upon systems of biologically derived interacting enzymes and coenzymes to function. The sterility indicator demonstrates that there is a direct correlation between the conditions to kill a microorganism and the conditions to inactivate a component of a network of interacting enzymes. In fact, the interactive system can be considered to mimic a bacterial spore in that there is a semi-permeable membrane, the spore wall, that encases a collection of interactive enzymes. In the case of an amplification interactive enzyme system, if any one of the key enzymes, coenzymes, cofactors, substrates, catalysts, or other reagent components of the system are totally inactivated when an indicator solution is added, no color change will occur, thus, mimicking conventional spore systems, but able to provide results at much faster speeds.

Using the test indicators of the invention, sterility verification is determined from completion of the test results which, surprisingly, can be very rapidly achieved because the reliability of conventional biological indicators is combined with the speed of techniques closer to that utilized by enzymatic and chemical indicators. Further, and unlike spores, resistance is correlated with activity, and in enzyme systems containing enzymes, coenzymes, catalysts, substrates or other reagents of an interactive system, stability can be very precisely quantitated individually as well as in multiple enzyme systems. Therefore, using interactive enzyme systems not only is speed increased, but a level of standardization can be achieved which is far superior to that obtained with conventional biological or other enzymatic techniques.

Another embodiment of the invention is directed to methods for the manufacture of adjustable indicator systems for the determination of the effectiveness of sterilization processes using steam, gas, radiation, chemical and plasma sterilizers, which are used in many hospitals, laboratories, and clinics, as well as in research institutions, in food and environmental laboratories, and in all technologies which utilize sterilization in manufacturing, production or waste disposal.

Sensitivity of sterility indicators can be adjusted quickly and easily for the manufacture of sterility indicators reactive to one or more predetermined parameters. For example, a test indicator substantially identical to the sterility indicator is exposed to a sterilization procedure and the effectiveness of that test indicator for reacting to the predetermined environmental parameter determined. The position and/or composition of the, for example, gas-transmissive plug of another test indicator is adjusted and another test indicator is exposed to the sterilization process. From the results determined for each test indicator, the sensitivity of the sterility indicator can be adjusted to optimize detection to the specific environmental condition or conditions.

Adjustments can be as simple as repositioning the gas-transmissive plug such as, for example, by extending or retracting an overhang portion of the plug, or by altering the composition of the plug by, for example, increasing or decreasing plug density, pore size or composition. The overhang portion could be extended to increase sensitivity of the indicator to a combination of increased temperature, humidity and pressure. A plug comprised of a compressible material can be adjusted by increasing the density of the compressible material to decrease sensitivity of the indicator to a combination of increased sterilant, chemicals, temperature, humidity and pressure.

A sterility indicator includes a biologically relevant material, such as bacterial spores or preferably a source of multiple interacting enzymes, in a container having a liquid impermeable and substantially gas non-adsorptive wall and at least one opening filled with a gas-transmissive barrier, said opening leading into a chamber which contains one or more components of the interactive enzyme system, with the gas-transmissive barrier between the components and the opening. Interactive components are preferably localized within close proximity to one another such as within the matrix of a cellulose filter disk or granulation product, and/or within a defined medium and are thus, coimmobilized. One or more enzymes, substrates, coenzymes or catalysts may be included on the solid matrix. Within the container is an effective amount of a gas-transmissive material to form the barrier which is semi-permeable, but not freely or wholly permeable to the transmission of liquids and gases, and an effective means for maintaining a finite distance between the semi-permeable opening and the enzymes. The barrier may be liquid permeable or impermeable, but is preferably a sponge which reduces the likelihood of slippage that may sometimes occur with plungers and stoppers. Also preferable is a barrier which is a plug that is constructed of a polymer such as a synthetic, a plastic, a rubber, Gore-Tex (a gas transmissive and liquid impermeable polymer) or a combination thereof. A Gore-Tex barrier would be liquid impermeable whereas an open cell foam barrier, such as a sponge, would be liquid semi-permeable.

Figure 1B:
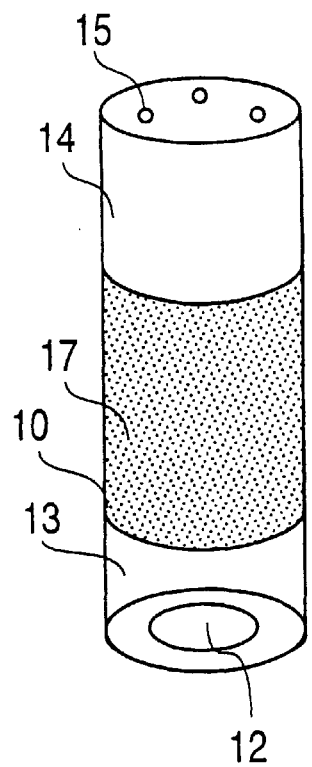

A rapid multiple enzyme sterility indicator of the invention is illustrated in FIG. 1. The indicator comprises cylindrical tube 10 having liquid impermeable walls with single opening 11 at one end. Cylindrical tube 10 contains solid support disk 12 upon which multiple interacting enzymes are coimmobilized. Cylindrical tube 10 also contains non-aqueous medium 13 covering solid support disk 12. Single opening 11 is covered with cap 14 having a plurality of holes 15 allowing unimpeded access of sterilant through single opening 11. The apparatus of FIG. 1 is assembled by placing solid support disk 12, upon which multiple interacting enzymes are coimmobilized, into the bottom of cylindrical tube 10. Non-aqueous medium 13 is added to cover solid support disk 12. A cylinder of heat resistant foam material 17 is compressed into cylindrical tube 10 providing a structural framework for the containment of non-aqueous medium 13. Foam material 17 also serves to maintain a fixed distance between the multiple interacting enzymes coimmobilized upon solid support disk 12 and single opening 11. Cap 14 is placed on top of cylindrical tube 10 covering single opening 11.

Figure 2:
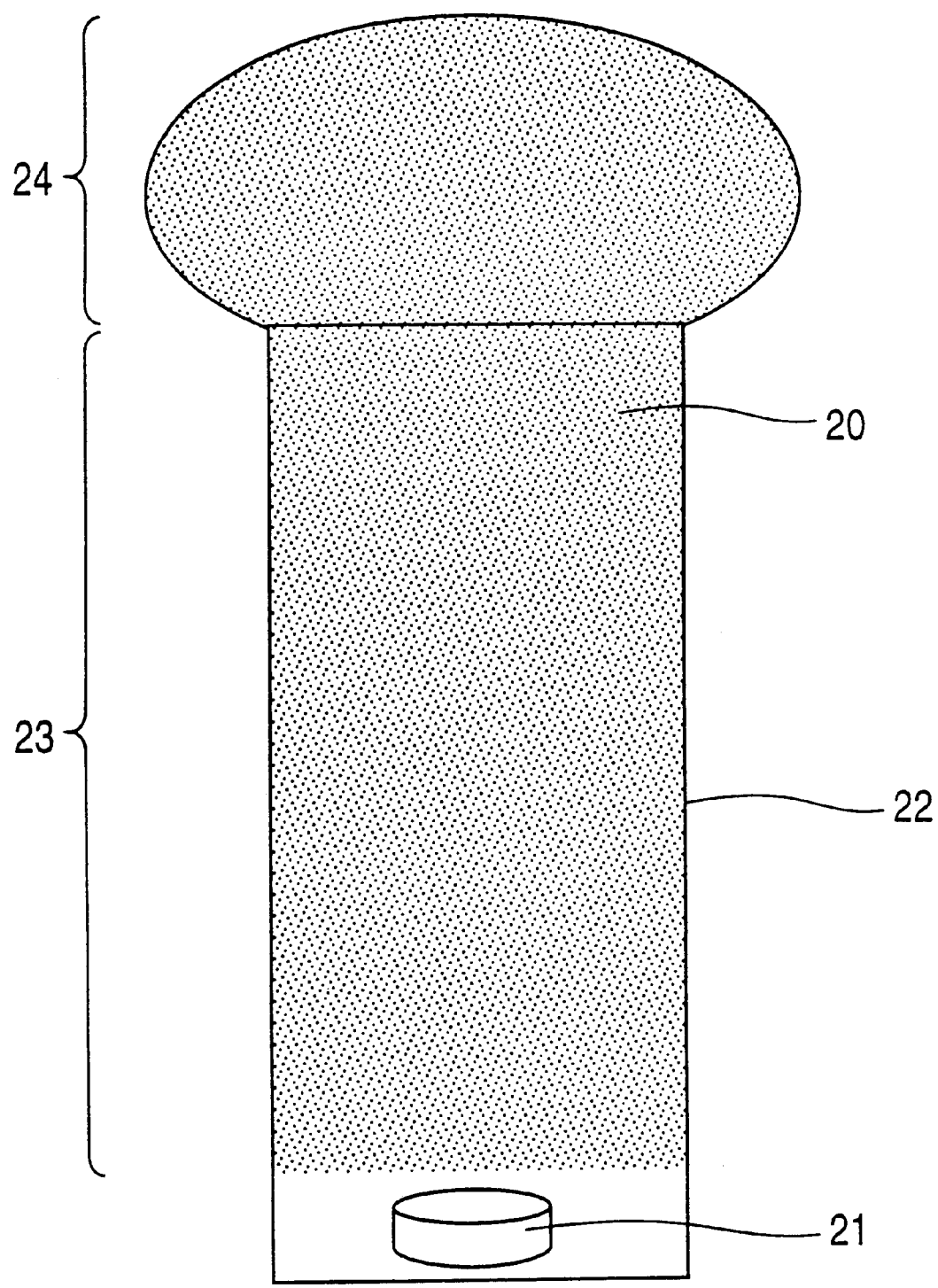
FIG. 2 A preferred embodiment of the rapid sterility indicator unit.

A preferred indicator unit of the invention is the rapid-multienzyme sterility indicator shown in FIG. 2. This multiple-enzyme sterility indicator comprises a test unit and indicator solution. The test unit is comprised of cylinder tube 22 having liquid impermeable walls with an opening at one end. Cylindrical tube 22 contains granulized tablet 21 comprising the coimmobilized interacting enzymes. The opening of the tube is filled with compressed foam insert 20. The foam material regulates the amount of sterilant reaching the tablet containing the interacting enzymes.

Figure 3A:
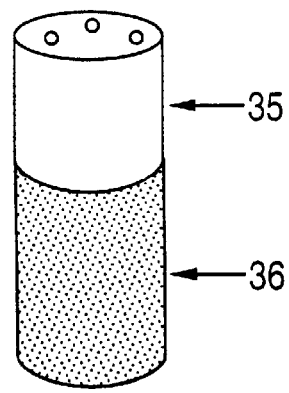
FIG. 3 Diagram of the preferred operation of a multiple-component container of a rapid sterility indicator.
Figure 3B:
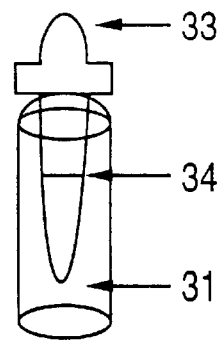
Figure 3C:
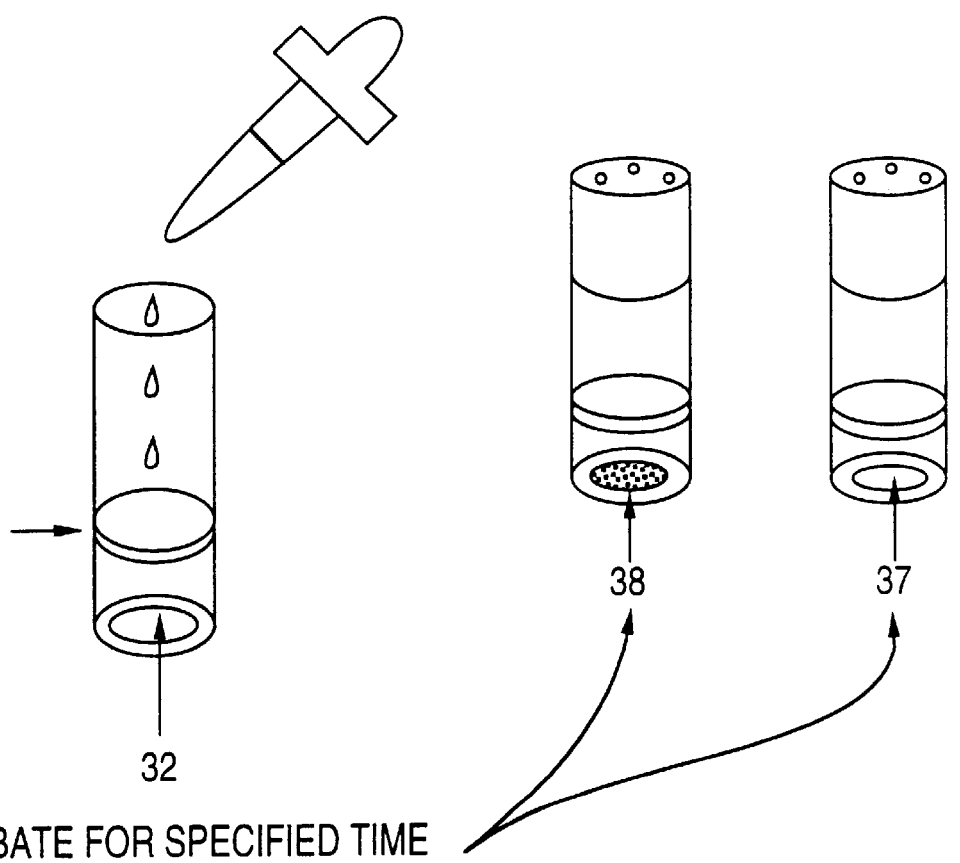

The dispenser of the indicator solution is shown in FIG. 3. A bottle contains indicator solution 31 which produces a visual color change when added to active multiple interacting enzymes coimmobilized on solid support disk 32. The bottle contains eyedropper 33 with premeasured volume line 34. Filling eyedropper 33 to premeasured volume line 34 with indicator solution 31 assures that the correct volume or number of drops of solution, is dispensed into the tube.

A method for conducting the sterility test is also illustrated in FIG. 3. The sterility indicator is placed into the sterilizer along with other materials which are to be sterilized. The sterility indicator is exposed to the sterilant during the course of a sterilization cycle. After the completion of the sterilization cycle, the sterility indicator is removed from the sterilizer and allowed to cool to room temperature. Cap 35 and foam material 36 are removed and can be safely discarded. Indicator solution 31 is drawn into eyedropper 33 using the premeasured volume line 34 to assure that the correct volume of indicator solution is used and dispensed into the tube. The resulting mixture is incubated, if necessary, at room temperature for seconds to minutes, preferably for less than about 10 minutes and more preferably for less than about 3 minutes. The solid support disk is visually inspected at the end of the incubation period. An absence of red coloration on the solid support disk (e.g., white) indicates negative result 37 and signifies a successful sterilization cycle. The presence of red coloration on the solid support disk indicates positive result 38 and signifies an unsuccessful sterilization cycle.

The sterilization procedure useful in the practice of the invention may be, for example, a steam-pressure procedure or autoclaving (121° C. or higher, such as 132° C. or 134° C.), a chemical procedure utilizing ethylene oxide or another appropriately lethal chemical or dry heat of temperatures between about 50° C. to about 200° C., or a plasma-phase sterilization procedure. These procedures are practiced in the health care industry, but also in industries having to do with environmental technology, food manufacturing, waste disposal and in those technologies where sterility is required.

Another embodiment of the invention is directed to an indicator for determining the effectiveness of a sterilant to pass through a tortuous path such as a challenge pack. Challenge pack testing, can make use of the same design and the same adjustable features. An AAMI steam challenge pack consists of a biological indicator such as bacterial spores on an inert carrier, wrapped in 16 surgical towels. The towels create a tortuous path for the steam to reach the indicator. This simulates the wrapped goods processed in a steam sterilizer in a hospital setting.

Figure 4:
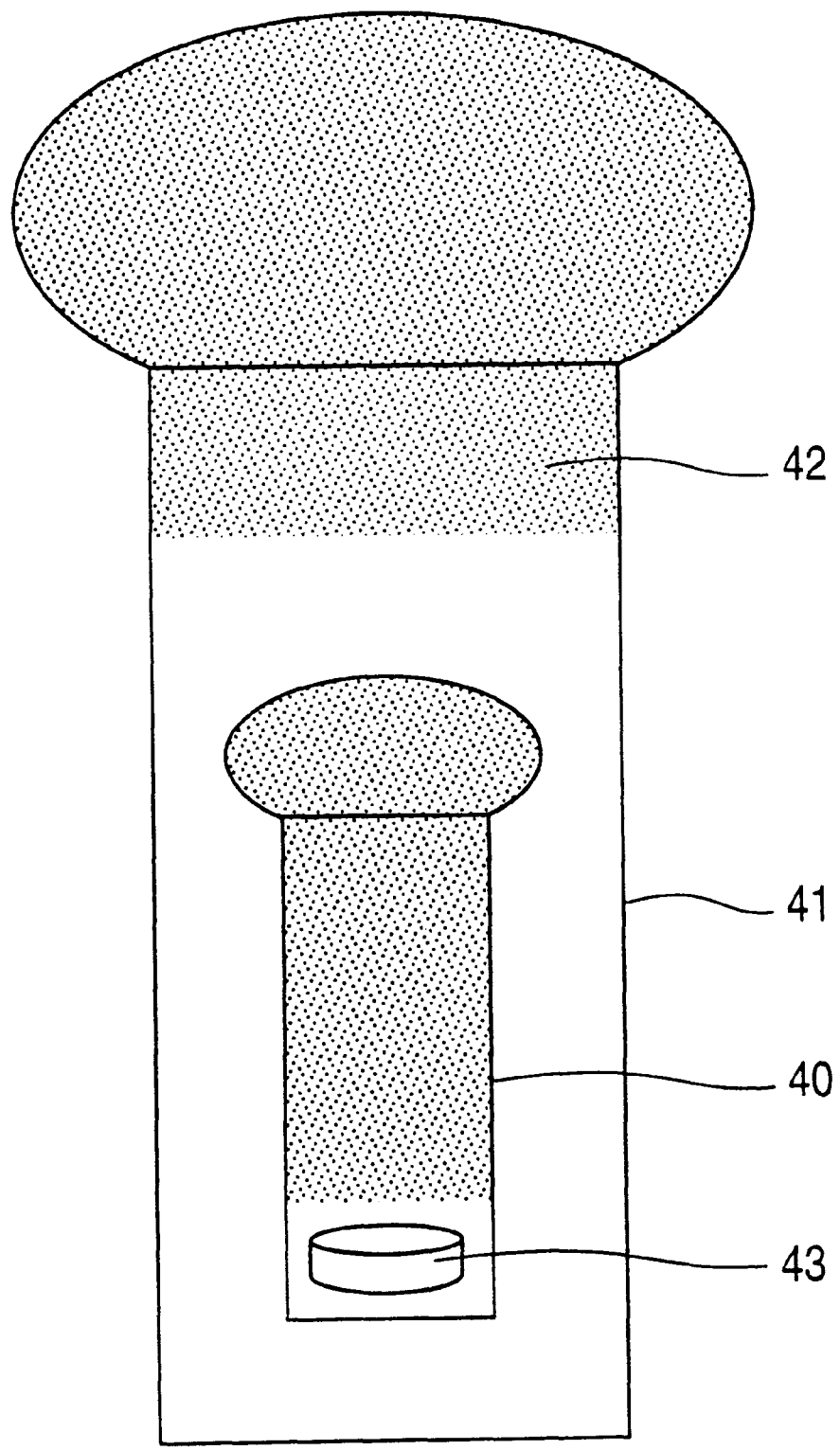
FIG. 4 Diagram of a challenge pack.

Challenge packs are used to test the effectiveness of the sterilant to pass through the pack and reach the indicator. This simulates wrapped goods processed in the sterilizer. The foam insert design can be used for challenge pack testing. A sterility indicator, either the enzyme-based indicator described previously or a conventional spore-based indicator may be used in this type of challenge pack. An example of a challenge pack is shown in FIG. 4.

Sterility indicator 40 is placed into container 41 which has at least one opening filled with a predetermined amount of foam 42. Container 41 has substantially gas non-adsorptive walls so the sterilant has to enter through foam 42 to reach sterility indicator 40 and thereby regulates the amount of sterilant entering the container. Sterility indicator 40 contains either spores or enzymes 43. Foam 42 regulates the amount of steam or sterilant entering the container. After the challenge pack has been exposed to the sterilization process, the indicator is removed from the challenge pack and processed. If the indicator is positive, proper sterilization conditions were not achieved within the pack. A negative result means proper conditions were met. The rapid sterility indicator described above or a standard biological indicator can be used in conjunction with the challenge pack. The challenge pack is simple to use and provides reproducible results. The desired amount of challenge can be easily reproduced to mimic the challenge described by standards such as AAMI, ISO or EN for a steam or ethylene oxide challenge pack.

Another embodiment of the invention is directed to the foam insert design for the air removal test. The air removal test consists of a container with a Bowie-Dick test sheet or a chemical indicator on a carrier. The transparent container consists of at least one opening which is filled with foam. After the test cycle is complete, the air removal test is removed from the sterilization chamber. The user observes the uniformity of the color change of the chemical indicator. Since the material of the container is transparent, the user would simply observe the uniformity of the chemical indicator ink. Thus, there is no need to unwrap the device.

The air removal test is also based on the similar design. By placing a chemical indicator into a transparent container with a foam insert, the prevacuum air removal test equivalent is made. The air removal test is placed into a prevacuum steam sterilizer. After the cycle is complete, the user can simply view the uniformity of the color change of the chemical indicator in the transparent container or simply open the container and remove the chemical indicator.

The foam insert design overcomes many disadvantages of the current designs for testing the effectiveness of sterilization processes. The foam insert design can be used as a component of a rapid sterility indicator composed of interactive enzyme systems which can provide nearly instantaneous results. A sterility indicator with the foam insert design also offers the advantage of being adjustable to suit various types of sterilization process. Presence of foam also allows the sterility indicator to effectively control the amount of sterilant entering the device in a standardized manner. The enzyme content of the rapid sterility indicator and the foam specifications can be easily controlled to provide reproducible results during manufacturing. Conventional biological indicators that are based on the inherent resistance of bacterial spores can not be as easily controlled.

The foam insert design also overcomes disadvantages of challenge pack and air removal test designs. Assembly of AAMI test packs is very time consuming. AAMI packs are not standardized in the sense that differences in how individuals make the packs and different types of towels can result in packs with differing characteristics. The advantages of the foam insert design is that it can be used for a sterility indicator for many types of sterilizers as well as challenge packs and air removal tests, it is simple to use and it is standardized and reproducible. The fact that the same design can be used for multiple tests (e.g., sterility, challenge packs, air removal) offers simplicity to the users. The challenge pack and air removal test designs also allow the user to quickly and easily retrieve the indicator. There is no need to unwrap many towels to retrieve the indicator. The transparent container also permits the user to confirm that an indicator is present in the pack.

Figure 5:
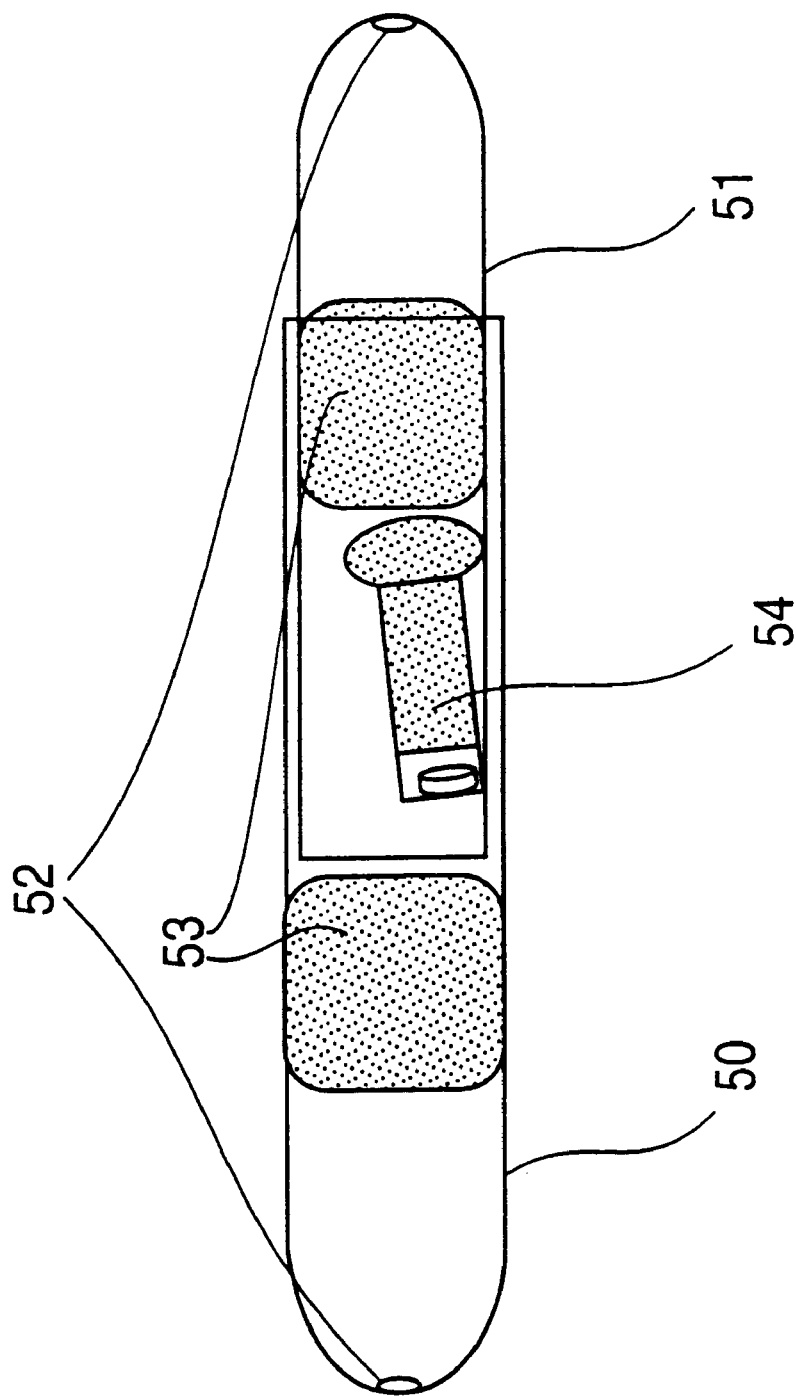
FIG. 5 A two container design challenge pack.

Another embodiment of the invention is directed to a method for determining the effectiveness of a sterilant to pass through a tortuous path comprises a challenge pack that employs the foam and container design that allows the users to easily open and close the challenge pack for repeated use. The challenge pack consists of two containers, two foam inserts and a sterility indicator, as shown in FIG. 5. Each container has at least two openings, one opening is the same size as the diameter of the container, the second opening is much smaller. One container 50 has a slightly larger diameter than the other container 51. Each container has a small hole 52 opposite the larger opening and a piece of foam 53 placed near the small opening. A sterility indicator 54 is placed into the smaller diameter container and the second container with a slightly larger diameter is placed over the first container's large opening. The containers fit together tightly due to their similar diameters. Instead of relying on the similar diameters to hold the two tubes together, a screw closure, a snap locking device or a twist locking device could be used. The containers have substantially gas non-adsorptive walls so that the sterilant has to enter through small holes 52 and pass through the foam inserts 53 to reach sterility indicator 54.

After the challenge pack has been exposed to the sterilization process, the two containers are dislodged from one another and the indicator is retrieved and processed as usual. This test pack can be used again by placing an unexposed indicator into one of the containers and replacing the second container over the first container as shown in FIG. 5. The sterility indicator can be the enzyme-based indicator or a conventional spore-based indicator.

Another embodiment of a reusable challenge pack design consists of a single container with one opening and a cap. A sterility indicator is placed into the container. The cap is made from a porous plastic material which allows steam to pass through. The capping device can be easily opened and closed by the user to retrieve the exposed indicator and add an unexposed indicator for the next test. The materials are a non-absorptive plastic which can withstand multiple exposures to sterilization.

Figure 6A:
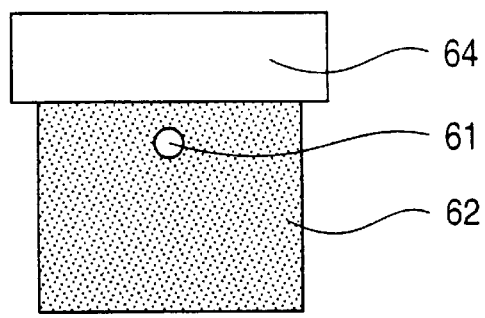
FIG. 6 Rapid sterility indicator test unit challenge pack design.
Figure 6B:
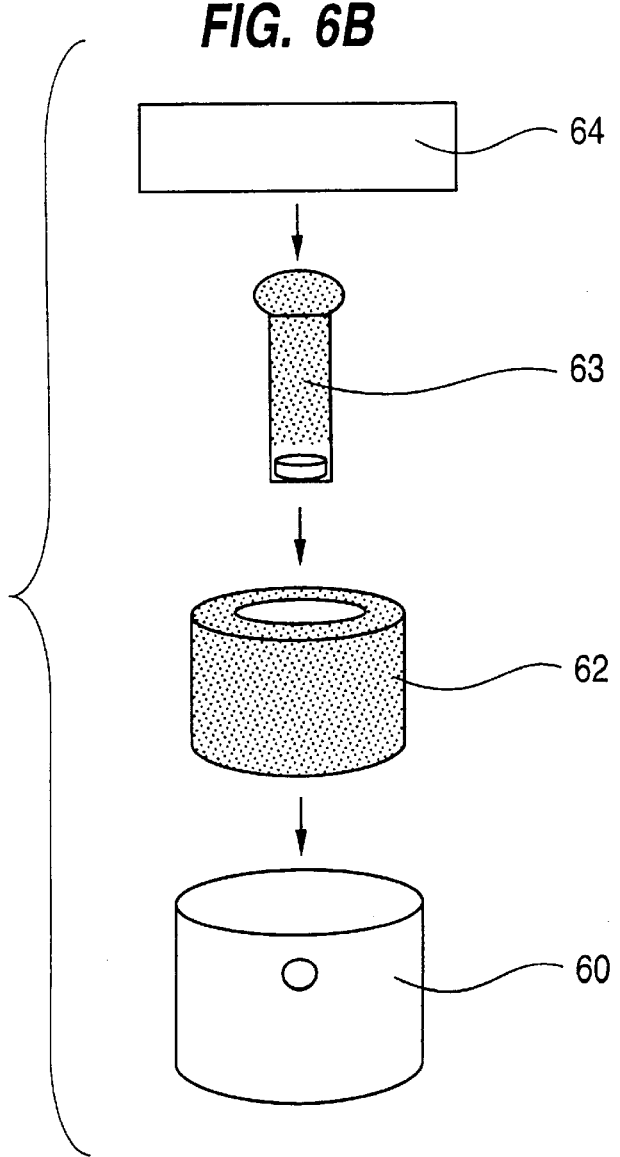

Another embodiment of a reusable challenge pack designs comprises a single container with a closure device, foam and a test indicator as shown in FIG. 6. The bottom portion of cylindrical container 60 has two holes 61 in the sides of the container. Tubular foam insert 62 fits tightly into the container. Foam insert 62 has a hole in the center which conforms to the shape of sterility indicator 63 which fits tightly into foam insert 62. Screw cap 64 is placed over the large opening of the container. When screw cap 64 is secured onto the container containing sterility indicator 63, sterilant would pass through the small openings in the sides of the container and through foam insert 62, before reaching sterility indicator 63. This is a tortuous path for the sterilant. This design would perform equivalent to other challenge packs. The materials are a non-absorptive plastic which can withstand multiple exposures to sterilization. The sterility indicator can be the enzyme-based indicator or a conventional spore-based indicator. By using a larger container and corresponding larger foam insert and replacing a chemical indicator (test sheet covered with unexposed chemical indicator ink) for the sterility indicator, this design could be used for air removal tests in pre-vacuum sterilizers. After processing in a pre-vacuum sterilizer, the uniformity of the chemical indicator color change would be used to determine if any air was present in the chamber. If air was present, the color change of the chemical indicator would not be uniform.

Another embodiment of the invention is directed to an apparatus for inserting compressible materials. Accuracy of the sterilization indicators depends on consistent placement of the foam plug in the container. Prior to the present invention, foam was placed in the container by hand, but unacceptably high incidence of improper placement results from this method. This invention provides apparatus for controlled positioning of foam in a container such as that present in the rapid sterility indicator. Various forms of the apparatus of this invention are shown in the drawings and described herein.

Figure 7:
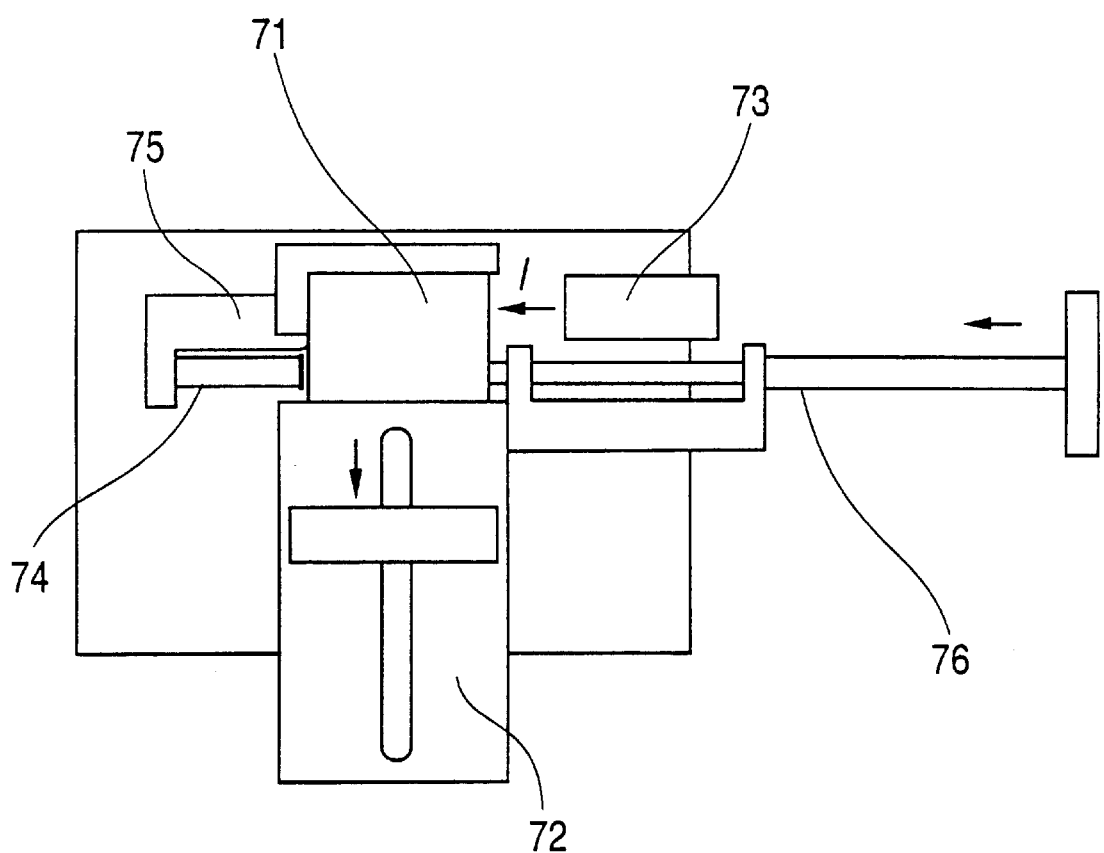
FIG. 7 A vertical front view of a machine incorporating a slide with a loop of flexible material to compress the foam and a plunger for insertion into the container.

FIG. 7 is a vertical front view of an insertion apparatus that compresses the resilient compressible material such as foam with a flexible strip of material 70 held in a loop configuration. The strip of material for the loop can be made from any flexible material such as Teflon, nylon, mylar or a thin sheet of steel preferably about 0.010 inches thick for a tight wrap. Initially, the two ends of the flexible material are nearly touching, forming a large loop. One end of the loop material is held at a fixed point, the other end is attached to horizontal slide 72. The large loop is the initial receptacle for the non-compressed material. The slide is pushed all the way to the left creating the loop with the largest diameter.

Non-compressed foam material 73 is placed into the large loop 70. Vial 74 is placed into holder 75. Slide 72 is pulled to the right by hand, cams, air cylinders or electric linear motion. As the slide is moving to the right, the loop becomes smaller and smaller in diameter, compressing the foam material into approximately ½ inch to ¼ inch or less of the original non-compressed diameter size. The foam is compressed in an efficient and reproducible manner. Compressed foam is plunged into the vial by vertical plunger 76 actuated by hand, cams, air and/or hydraulic cylinders or electric linear motion actuator. Plunger 76 backward extrudes the compressed foam material 73 into vial 74. The drawing shows holder 75 that indexes 90 degrees. In this manner, foam material 73 is efficiently deposited into vial 74. The apparatus can be adjusted to deposit the foam all the way into the vial, to a desired depth, or to leave a desired amount of foam protruding past the opening. The depth of the stroke of the vertical plunger regulates the position of the foam. The path of the vertical plunger is within the flexible loop regardless whether the loop is open or closed.

Figure 8A:
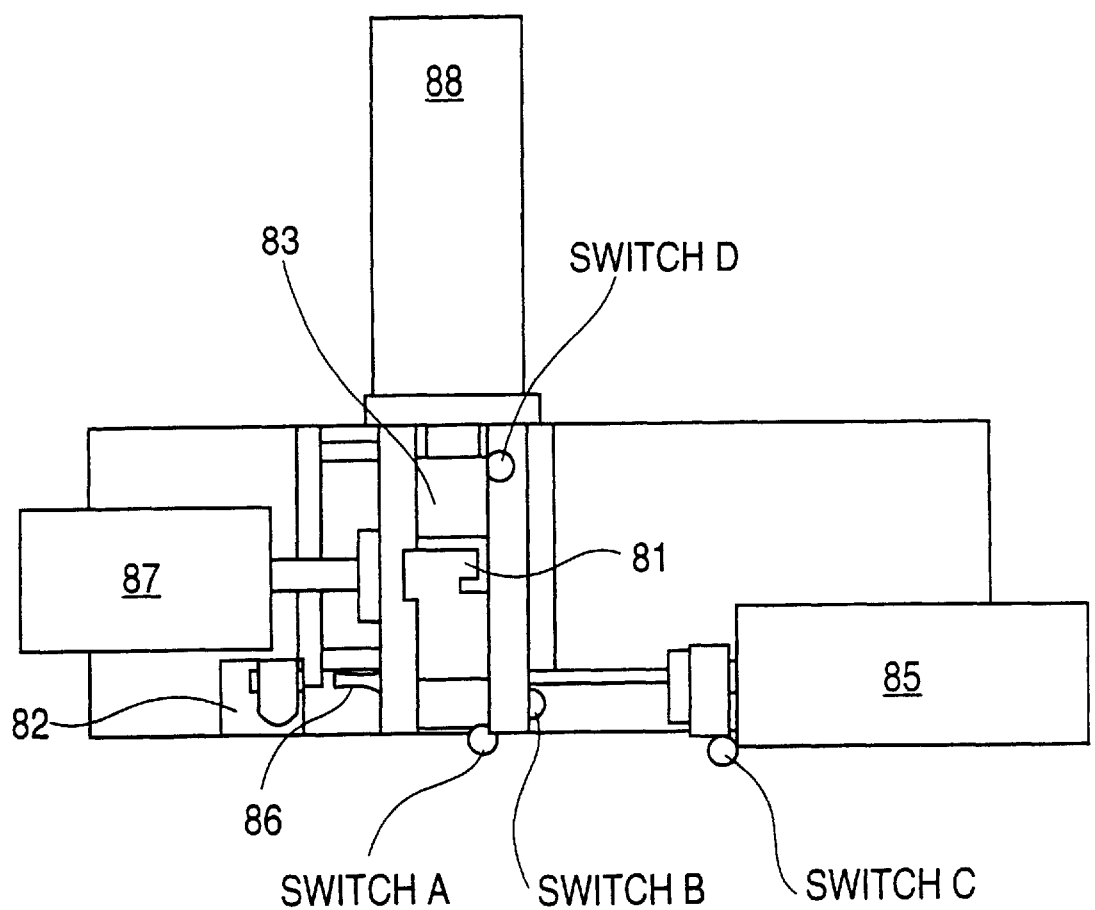
FIG. 8 (A) A vertical front view of a machine with a horizontal crusher slide to compress the material and a vertical plunger and staging nozzle used for insertion, and (B) a side view of the angular forming die to compress the material prior to insertion.

FIG. 8A is a vertical front view of a machine to compress resilient material and deposit it into a container. A foam cylinder is placed into slide chamber 81 and the vial is placed into vial block 82. Angular crusher slide 83 strokes to compress resilient material 84. As the angular crusher slide assembly advances, the foam is rolled into a fraction of the original diameter (FIG. 8B). Angular crusher slide 83 provides a single moving part which compresses resilient material 84 and ultimately forms a compression chamber holding the material in compressed state. Plunger cylinder 85 stokes downward, plunging the compressed material into staging nozzle 86 which is a hollow tube. Staging nozzle 86 with the compressed foam is partially inserted into the vial by stripper cylinder 87. Staging nozzle 86 is retracted while plunger cylinder 85 remains stationary causing the foam to be deposited into the vial. Plunger cylinder 85 retracts as a blast of air is forced into crusher slide cylinder 88 clearing any debris. Adjustments can be made to place the foam at any depth within the vial, including leaving a portion of foam protruding from the vial opening.

The apparatus of FIG. 7 and FIG. 8 represent alternative devices for carrying out the same method of inserting foam into a vial, whereby a foam insert is compressed into a cylinder in a first step and the compressed foam is positioned in a vial in a second step. Horizontal slide 72 can be replaced with angular crusher slide 83 that is a more positive mechanism. The reverse of the above is also true as angular crusher slide 83 can be replaced by horizontal slide 72.

FIG. 9 depicts another method of inserting a compressible resilient material into a vial, by rotating the vial over the stationary piece of foam. One end of foam 91 is placed slightly into vial 92 which is held by flexible tube 93 connected to a rotating device comprised of bearing block and fixture base 94. The other, opposite end of the foam is held and fed into the rotating vial. As vial 92 rotates, foam 91 is inserted into the vial with a helix effect. The device can be rotated with crank 95 by hand, by air cylinders or by electric linear motion actuator. An indexing machine can be added to the above combined fixtures and/or stations. The fixture for rotation can be applied to the index disc which may have an annular slot enabling a rubber wheel to rotate the vial contained on the circumference of the indexing disc.

The following examples illustrate embodiments of the invention, but should not be viewed as limiting the scope of the invention.

EXAMPLES

Example 1

Rapid Sterility Indicator for Monitoring Steam Sterilization Process

A rapid sterility indicator for steam sterilization is composed of a test unit and indicator solution. The test unit is composed of a cylindrical glass vial, a tablet containing components of a plurality of interacting enzyme systems, a foam insert, and a label. The glass vial is approximately ¼ inches in diameter and 1 inch high, open on one end.

The tablet containing two interactive enzymes of the enzyme system is placed into the vial. The tablet is a granulation of glucose dehydrogenase and diaphorase. The preferred enzyme concentration for each enzyme is 8 to 15 units per 20 mg tablet. The opening of the vial is filled with a compressed foam insert. The foam insert is preferably a cylinder, with a diameter range of ¼ to 1 inch, preferably approximately ½ inch and the length range ⅛ to 3 inches preferably approximately 1½ inches in length. Foam is partially open celled with a density of approximately 6 pounds per cubic foot and the foam material is polyurethane. The detailed specifications include: polyester foam, open cell, 6 lbs, charcoal color, density is 5.00–6.60 p.c.f, strength 20.0–40.0 p.s.i., elongation 300–500%, tear resistance is 3.0–5.0 p.l.i., compress set 3.0 to 10.0%, load defection, 0.50 to 0.90 p.s.i., flammability HF-1, and cell size 50–70 c.d.i. On the outside of the vial was a label containing steam-sensitive indicator ink.

This test unit was placed into the sterilization chamber of a steam sterilizer operating at 121° C. along with the items to be sterilized. After the cycle is complete, the test unit was removed from the sterilization chamber. The color change of the steam-sensitive indicator ink serves to identify the processed units from unprocessed units. The foam insert was removed and five drops of the clear, colorless indicator solution was added to the vial containing the white enzyme tablet. The indicator solution was packaged in an amber glass bottle with a dropper dispenser. The indicator solution contains p-iodonitrotetrazolium violet within a range of 32 $\mu$M to 16 mM, preferably 3.2 mM; NAD ($\beta$-nicotinamide adenine dinucleotide) within a range of 1 $\mu$M to 5.5 mM, preferably 0.11 mM; glucose within a range of 1% to 90% preferably 10%; ethanol within a range of 1% to 95% (by volume), preferably 5.5%; citric acid within a range of 0.0032 mm to 3.2 m, preferably 17 mm. The preferred buffer was 0.05 M Tris, pH 6.0–8.5.

The predetermined survival cycle in a BIER vessel operating at 121° C. was 5 minutes, the kill cycle was 15 minutes for sterility indicators. Survival cycles were cycles with short exposure times in which indicators should test positive, indicating proper sterilization conditions were not met. Kill cycles were usually the standard cycles times in which the indicator should test negative indicating proper sterilization conditions were met. After indicator solution was added to the white tablet, the color of the tablet was visually observed for 1 to 20 seconds. After a 5 minute autoclave survival cycle at 121° C., which represents inadequate sterilization conditions, a positive result was expected and observed, in which the enzymes are active and a red colored product was formed on the surface of the tablet at or before 20 seconds. After a 15 minute autoclave kill cycle at 121° C. which represents an adequate sterilization cycle, a negative result was expected and observed, in which one or more enzymes were inactivated and no red colored product was formed. These positive and negative results parallel the results of bacterial spores exposed to similar conditions in a steam autoclave.

TABLE 1

Steam Sterilization Test in a BIER Vessel

|  | Survival Time (5 minutes) | Kill time (15 minutes) |
|---|---|---|
| Rapid Sterility Indicator | 10/10 | 0/10 |
| Sportrol spore strips (10$^6$ B. stearothermophilus) | 10/10 | 0/10 |

Table 1 shows results from a typical experiment. Results are recorded as the number of positives over the number tested (121° C.) in a BIER vessel. Rapid sterility indicators provided both positive results after the survival cycles and negative results after the kill cycles. These results demonstrate the at least equivalence of rapid sterility indicators to conventional biological indicators.

Example 2

Effects of Foam Structure, Size and Position

Test units as described in Example 1 were prepared by inserting into the vial foam inserts from various suppliers, all of which were 6 lbs. per cubic foot foam. In some of the test units, foam was inserted until none protruded above the end of the vial, while in others, foam was left to extend outside the vial from 0:125–0.5 inches. Other parameters were as in Example 1, and test units were exposed to 121° C. for 5 minutes in a BIER vessel. After the cycle, foam was removed, indicator solution was added and color read after 30 seconds.

TABLE 2

Foam Positioning Effects at 121° C.
Foam cylinders, approximately: 1.5" long, 0.5" diameter, 6 lbs density

|  | Positives after 5 min. exposure to 121° C. | Percent Positives |
|---|---|---|
| no overhang | 43/59 | 73% |
| ¼" overhang | 37/58 | 64% |
| ½" overhang | 5/21 | 24% |

Results in Table 2 show the effect of the foam position within the vial. The number of positive results (pink tablet) was recorded over the total number tested. As the amount of foam protruding past the vial increased, the amount of foam compressed within the vial decreased. As the amount of compressed foam decreased, more sterilant is able to pass through the foam and inactivate the enzymes in the tablet. Fewer positives are seen as the overhang increases. These tests were performed using several different types of 6 lbs. foam and the foam was often cut into cylinders by hand. The consistency of the results increased greatly when the foam was from a single supplier and was cut into cylinders using reproducible methods such as using a water jet or using dies, though foam position still has an effect on the results as seen in Table 5.

Test units as described in Example 1 were prepared by inserting foam cylinders approximately 1.5 inches long and 0.5 inches in diameter. Two different foam densities were tested, a 6 lbs. per cubic foot foam and a 2 lbs. per cubic foot foam, both open celled with a ¼ inch overhang. Test units were exposed to 121° C. in a BIER vessel for a 5 minute (survival) cycle. The number of positive results (pink tablet) was recorded over the total number tested. Color was recorded after 20 seconds.

TABLE 3

Effects of Foam Density
Foam cylinders of approximately 1.5 inches long, 0.5" diameter

|  | Survival after 5 min. Exposure to 121° C. | Percent Positives |
|---|---|---|
| 6 lbs foam | 20/20 | 100% |
| 2 lbs foam | 0/20 | 0% |

The results of Table 3 show that foam density also plays a key role in regulating the amount of sterilant that reaches the tablet. The 6 lbs. foam, used in the prescribed configuration, produced all positives. The same shaped foam of a 2 lbs. density allowed the steam to pass through and inactivate the tablet. Foam density as well as the foam length and overhang amount can be adjusted to provide the desired results for the intended type of sterilization process.

Example 3

Prevacuum Sterilization

An alternative sterilization protocol involves pre-evacuation of the sterilization chamber followed by a shorter period of exposure to steam at a higher temperature (132° C. or 134° C.). The predetermined survival/kill cycle times for a 132° C. and 134° C. pre-vac sterilizer is 20 seconds/3.0 minutes, respectively. Test units according to Example 1 were processed in the prevacuum mode, and the results are shown in Table 4.

TABLE 4

Steam Sterilization Test in a Prevacuum Sterilizer using 132° C. and 134° C. Steam

|  | Survival Time | Kill time |
|---|---|---|
| Rapid Sterility Indicators (1.32° C.) | 10/10 | 0/10 |
| Sportrol spore strips (132° C.) ($10^6$ B. stearothermophilus) | 10/10 | 0/10 |
| Rapid Sterility Indicators (134° C.) | 10/10 | 0/10 |
| Sportrol spore strips (134° C.) ($10^6$ B. stearothermophilus) | 10/10 | 0/10 |

Results in Table 4 are recorded as the number of positives over the number tested. The indicator reaction was read at 20 seconds. These results show that the rapid sterility indicators met the predetermined survival/kill parameters for a 132° C. and 134° C. prevacuum steam sterilizer, at least equivalent to biological indicators. The Rapid Sterility Indicators, as described in Example 1, can effectively monitor both 121° C. gravity and 132° C./134° C. pre-vac sterilization cycles.

In a subsequent test, foam inserts of the same size were placed into Test Units with 1/8", 1/4", 3/8", 1/2" and 9/16" overhang and were then subjected to the 132° C. pre-vacuum survival/kill test. Forty test units with each specified overhang (total of 200 test units) were assembled. For each overhang test length, 2 sets of 10 test units were exposed to a survival cycle, and two sets of 10 were exposed to a kill cycle.

TABLE 5

Positioning effect for 132° C.

| Foam Position (overhang) | Results after exposure to a survival cycle (20 seconds) | Results after exposure to a kill cycle (3 minutes) |
|---|---|---|
| 1/8" | 10/10 | 0/10 |
| 1/8" | 10/10 | 0/10 |
| 1/4" | 10/10 | 0/10 |
| 1/4" | 10/10 | 0/10 |
| 3/8" | 10/10 | 0/10 |
| 3/8" | 10/10 | 0/10 |
| 1/2" | 0/10 | 0/10 |
| 1/2" | 0/10 | 0/10 |
| 9/16" | 3/10 | 0/10 |
| 9/16" | 4/10 | 0/10 |

Table 5 shows that the foam insert overhang of the rapid sterility indicator can range from 1/8" to 3/8" without the results being significantly affected. The specification for assembly of the rapid sterility indicator is set at 1/4±1/8" (1/8" to 3/8"). After a survival cycle the enzyme tablet is positive (pink to red) and after a kill cycle the enzyme tablet is negative (white).

If the foam overhang length is greater than 3/8", the indicator does not provide 100% survival after exposure to the 20 second survival cycle. The foam position plays a critical role. The foam overhang must be within the defined specifications for the indicator to function properly.

Example 4

Foam Structures to Mimic AAMI Challenge Packs

AAMI challenge packs provide a tortuous path for steam penetration. An analogous challenge pack for a steam sterilizer can be created using a container, foam, and a rapid sterility indicator (as described in Example 1) or a biological indicator. The challenge pack container is a plastic or glass tube, preferably plastic, measuring approximately 1.125 inch diameter and 5 inches in length with one opening in the container. The container contains a heat sink material such as a metal object. In this case a rapid sterility indicator test unit, as described in Example 1, is placed into the container. The one opening of the container is filled with a foam insert. Foam insert is approximately 2 to 4 inches in diameter and 1 to 4 inches long (non-compressed measurements). Foam is partially open celled with a density of approximately 1 to 6 pounds per cubic foot and foam material is preferably polyurethane.

Challenge packs are placed into a steam sterilizer operating at 121° C. or 132° C. and exposed to the predetermined survival and kill time intervals. Survival cycles are cycles with short exposure times in which indicators should test positive, indicating proper sterilization conditions were not met. Kill cycles are the standard cycles times in which the indicator should test negative indicating proper sterilization conditions were met. The rapid sterility indicators are processed as described in Example 1, the results are obtained at 20 seconds or less after adding indicator solution.

The AAMI challenge pack is constructed and tested for comparison. The materials required for a AAMI challenge pack for a steam sterilizer are 16 freshly laundered huck towels, autoclave tape, and sterility indicators. Each towel is folded lengthwise into thirds and the folded width-wise in half Towels are placed one on top of another with the folds opposite each other. Rapid sterility indicators and conventional biological indicators are placed between the eighth and ninth towels. The pack is secured with autoclave tape. The AAMI steam challenge packs are placed into a steam autoclave at 121° C. for the appropriate amount of time. After the cycle, indicators are processed as in Example 1.

TABLE 6

Challenge Pack Analog

|  | Exposure time to 121° C. steam | |
|---|---|---|
|  | Survival Time for Challenge Packs (10 minutes) | Kill time for Challenge Packs (30 minutes) |
| Rapid Sterility Indicators in Foam Challenge Packs | 6/6 | 0/6 |
| Rapid Sterility Indicators in AAMI Challenge Packs | 6/6 | 0/6 |
| Sportrol Spore Strips ($10^6$ B. stearothermophilus) in AAMI Challenge Packs | 6/6 | 0/6 |

The results in Table 6 are recorded as the number of positives over the number tested. As shown, when exposed to the survival cycle time, all indicators tested positive. When exposed to the kill cycle time, all indicators tested negative. This table also shows the equivalence of the conventional biological indicators in AAMI challenge packs to the rapid sterility indicators in AAMI challenge packs. These results demonstrate the equivalence of the rapid sterility indicator in the foam challenge pack to the AAMI steam challenge pack.

Example 5

Rapid Sterility Indicator in a Plasma-Phase Hydrogen Peroxide Sterilizer

The rapid sterility indicator as described in Example 1 was used with one modification, the preferred foam length was changed from 1.5 inches to 0.375 inches. Rapid sterility indicators were exposed to survival and kill cycles in the plasma-phase sterilizer. Survival cycles are cycles with short sterilant diffusion times in which indicators should test positive, indicating proper sterilization conditions were not met. Kill cycles are the standard cycles times in which the indicator should test negative indicating proper sterilization conditions were met.

The survival time for the plasma-phase hydrogen peroxide sterilizer was determined to be a 6 minute diffusion time. Plasma time was held constant at 15 minutes and vaporizer time was 4 minutes. Kill time was determined to be a 50 minute diffusion time. Rapid sterility indicator test units were placed into the sterilizer and exposed to the survival and kill cycles and processed as in Example 1. Results were recorded 10 seconds after adding the indicator solution to the test unit.

TABLE 7

Plasma-phase $H_2O_2$ Sterilizer Survival/Kill Times

| Foam Length | Survival[1] | Kill[2] |
|---|---|---|
| No Foam | 0/5 | 0/5 |
| 0.375" | 5/5 | 0/5 |
| 0.75" | 5/5 | 5/5 |
| 1.50" | 5/5 | 5/5 |

TABLE 8

Plasma-phase $H_2O_2$ Sterilizer-Partial Cycle Times

| Foam Length | Survival[3] | Kill[4] |
|---|---|---|
| No Foam | 0/5 | 0/5 |
| 0.375" | 2/5 | 0/5 |
| 0.75" | 5/5 | 5/5 |
| 1.50" | 5/5 | 5/5 |

1=Diffusion time 6 minutes; Plasma time 15 minutes; Vaporizer time 4 minutes; and Readout time 10 seconds
2=Diffusion time 50 minutes; Plasma time 15 minutes; Vaporizer time 4 minutes; and Readout time 10 seconds
3=Diffusion time 8 minutes; Plasma time 15 minutes; Vaporizer time 4 minutes; and Readout time 10 seconds
4=Diffusion time 10 minutes; Plasma time 15 minutes; Vaporizer time 4 minutes; and Readout time 10 seconds In the tests shown in Tables 7 and 8, the rapid sterility indicator showed a graded response to the STERRAD sterilizer. By adjusting the foam length, the desired survival/kill times could be met. This demonstrates that the rapid sterility indicator can be used to test the effectiveness of the STERRAD hydrogen peroxide sterilizer. The foam length of 0.375 inches provided the proper survival/kill results at 10 seconds after addition of the enzyme system reagents. Further testing would further define the optimal foam density, foam length and foam insert overhang for a sterility indicator.

These tests demonstrate that the rapid sterility indicator is effective for monitoring the plasma-phase hydrogen peroxide sterilizer. All positives were observed after the survival time and all negatives were observed after the kill time.

Example 6

A Two Container Reusable Pack to Mimic AAMI Challenge Packs

A reusable challenge pack can also be used to mimic an AAMI Challenge pack. A challenge pack can be created from two containers, two pieces of foam and a sterility indicator. A reusable challenge pack is made of material which can withstand multiple exposures to sterilization and can be easily opened and closed. The containers are made from plastic or glass, preferably plastic. One container is approximately 7/8" diameter, 3.5" long. The diameter of one opening is 7/8", the diameter of the second opening at the opposite end of the container is 13/64". The second container is approximately 1 1/8 diameter, 4" long. The diameter of one opening is 1 1/8", the diameter of the second opening at the opposite end is 13/64". A cylindrical piece of open cell, 2 pound polyurethane foam approximately 1" long and 1" diameter is placed into each container, not more than 1" from the smaller opening. The rapid sterility indicator test unit as described in Example 1 is placed into one of the containers, on top of the foam. The 7/8" diameter opening of the one container is placed into the 1 1/8" diameter opening of the second container. The containers fit together tightly so that the only pathway for steam to enter the challenge pack is through the small openings, passing through the foam inserts to reach the indicator. The pack may also contain a beat sink material such as a metal object.

Challenge packs were placed into a steam pre-vac sterilizer operating at 132° C. and exposed to the predetermined survival and kill cycles. Survival cycles are shorts exposures times in which the indicators should test positive indicating the proper sterilization conditions were not met. A 30 second cycle time in a 132° C. pre-vacuum sterilizer is an example of a survival time for indicators in challenge packs. An example of a kill cycle time in a 132° C. pre-vacuum sterilizer is 3.5 minutes. After the kill cycle indicators should test negative indicating proper sterilization conditions were met. After the cycles were complete, the containers were dislodged from one another and the indicator retrieved. The rapid sterility indicators were processed as described in Example 1, the results are obtained at 20 seconds or less after adding the indicator solution.

TABLE 9

Two Container Reusable Challenge Pack

| | Exposure time to 132° C. steam, pre-vac. sterilizer | |
|---|---|---|
| | Survival Time for Challenge Packs (30 seconds) | Kill Time for Challenge Packs (3.5 minutes) |
| Rapid Sterility Indicators in two container reusable challenge pack | 7/7 | 0/7 |

The results in Table 9 are recorded as the number positive over the number tested. As shown, when exposed to a survival cycle, all indicators tested positive. When exposed to the kill cycle time, all indicators tested negative. This table shows that the challenge pack designs provides acceptable results. This challenge pack also has the unique feature such that the user can reassemble the pack by placing a new indicator into the container, close the container, and use it for another test. This design could be reused multiple times.

Example 7

A Single Container Reusable Pack to Mimic AAMI Challenge Packs

A reusable challenge pack can be created from one container with a closure device, one piece of foam and a sterility indicator. A reusable challenge pack is made of material that can withstand multiple exposures to sterilization and can be easily opened and closed. The container is made from plastic or glass, preferably plastic. The container is approximately 1½" diameter, 2½" long with a screw cap. The two steam entry holes are approximately ¼" in diameter and the holes are located approximately ¼" below the cap. A tubular piece of open cell, 2 pound polyurethane foam approximately 1½" long, 1½" outer diameter (inner diameter ⅜") is placed into the container. The rapid sterility indicator test unit as described in Example 1 is placed into the foam insert. The foam fits tightly into the container and the test unit fits tightly into the foam. The cap of the container is screwed into place and creates a tight seal so that the only pathway for steam to enter the challenge pack is through the small openings, passing through the foam to reach the indicator. The pack may also contain a heat sink material such as a metal object.

These challenge packs were placed into a steam sterilizer operating at 132° C. (pre-vac sterilizer) and 121° C. (gravity) and exposed to the predetermined survival and kill cycles. After the kill cycle indicators should test negative indicating proper sterilization conditions were met and the indicators should be positive after the survival cycles. After the cycles were complete, the container was opened and the indicator retrieved. The rapid sterility indicators were processed as described in Example 1, the results are obtained at 20 seconds or less after adding the indicator solution.

TABLE 10

One Container Reusable Challenge Pack

| | Survival time/Kill time 132° C. Steam Sterilizer | | Survival time/Kill time 121° C. Steam Sterlizer | |
|---|---|---|---|---|
| | (1 min.) | (4 min.) | (10 min.) | (30 min.) |
| Rapid Sterility Indicators in one container reusable challenge pack | 7/7 | 0/7 | 3/3 | 0/7 |

| | 132° C. Steam Sterilizer | | 121° C. Steam Sterilizer | |
|---|---|---|---|---|
| | 1 min. | 4 min. | 10 min. | 30 min. |
| Rapid Sterility Indicator in one container reusable challenge pack | 20/2 | 0/20 | 20/20 | 0/20 |

The results in Table 10 are recorded as the number positive over the number tested. As shown, when exposed to a survival cycle, all indicators tested positive. When exposed to the kill cycle time, all indicators tested negative. This table shows that the challenge pack design provides acceptable results. This challenge pack also has the unique feature such that the user can reassemble the pack by placing a new indicator into the container, closing the container, and using it for another test. This design can reused multiple times.

Example 8

Automated Compression and Insertion

Using the apparatus depicted in FIG. 8A, a labeled glass vial (about 8 mm in diameter and about 30 mm in length) containing a test tablet (about 5 mm in diameter and about 2 mm in length) is placed into the vial block. A polyurethane foam cylinder (about 15 mm in diameter and about 40 mm in length) is placed into slide chamber 81. Angular crusher slide assembly 83 advances, the foam is compressed to about one fourth the diameter of the non-compressed size. Plunger cylinder 85 stokes downward plunging the compressed foam into staging nozzle 86 which is a hollow tube. Staging nozzle 86 with the compressed foam is partially inserted into the vial by stripper cylinder 87. Plunger cylinder 85 pushes the foam into the vial while staging nozzle 86 is retracted and foam is deposited into the vial. Plunger cylinder 85 retracts as a blast of air is forced into the crusher slide chamber, clearing any debris. The foam is protruding past the vial approximately one quarter inch. The amount of foam inserted into the vial can be adjusted.

Example 9

Comparison of Manual and Mechanical Insertion

The Test Unit of the rapid sterility indicator for steam sterilization consists of a glass vial, enzyme tablet and foam insert. Historically, the foam insert was placed inside the glass vial manually. Manual assembly is achieved by twisting and pushing the foam insert inside the vial opening until the foam overhang is within the required specification of 0.125–0.375 inches. To facilitate faster production of the test units, an automated foam stuffer has been manufactured by Custom Machine, Inc. (Kansas, Ohio).

The apparatus of FIG. 8 placed a hollow stainless steel tube inside the glass vial (already containing the enzyme tablet), squeezed the foam vertically and, via forced air, pushed the condensed foam inside the stainless steel tube. The stainless steel tube was removed from its original position leaving the foam. Condensed foam occupied the space allowed inside the glass vial. The automated machine did not use twisting action as the means for foam insertion.

Performance of the test units, when packaged manually, was compared to the performance of the test units packaged via the automated procedure. Testing involved steam exposure in a BIER vessel at 5, 7, 8, 9, 10, 11, 12, 13 and 15 minutes on three different lots of test units packaged both manually and using the automated procedure. The product packaged automatically also had 5 minute and 15 minute testing in an autoclave. In addition, the foam overhang of the test units packaged automatically were measured to ensure they met the required specification of 0.125–0.375 inches.

Three lots of test units were manually packaged, 100 per lot. Each lot consisted of a different configuration of tablet lot and foam lot. Test units were labeled Lot A, Lot B and Lot C. Two hundred glass vials were labeled as Lot A, Lot B and Lot C. These were the glass vials used for the automated procedure. Using the automated procedure, 200 test units for each lot (A, B and C) were packaged.

The overhang was measured, using calibrated calipers, on 80 automatically packaged test units from each lot, and the results are shown in Table 11. Measured foam overhang of the sampled test units were all within the range of 0.125–0.375 inches.

TABLE 11

Measurement of Foam Overhang in Inches

| Lot A | | Lot B | | | | Lot C | | |
|---|---|---|---|---|---|---|---|---|
| 0.257 | 0.302 | 0.312 | 0.248 | 0.242 | 0.247 | 0.289 | 0.254 | 0.257 |
| 0.371 | 0.336 | 0.337 | 0.254 | 0.247 | 0.266 | 0.299 | 0.295 | 0.255 |
| 0.288 | 0.278 | 0.320 | 0.249 | 0.240 | 0.239 | 0.278 | 0.303 | 0.290 |
| 0.274 | 0.304 | 0.312 | 0.241 | 0.243 | 0.252 | 0.298 | 0.319 | 0.299 |
| 0.307 | 0.285 | 0.296 | 0.253 | 0.238 | 0.244 | 0.319 | 0.283 | 0.257 |
| 0.326 | 0.312 | 0.300 | 0.241 | 0.241 | 0.240 | 0.274 | 0.250 | 0.250 |
| 0.302 | 0.311 | 0.287 | 0.235 | 0.253 | 0.235 | 0.313 | 0.300 | 0.266 |
| 0.285 | 0.294 | 0.284 | 0.250 | 0.247 | 0.238 | 0.268 | 0.291 | 0.258 |
| 0.322 | 0.258 | 0.308 | 0.254 | 0.232 | 0.250 | 0.275 | 0.281 | 0.312 |
| 0.271 | 0.288 | 0.320 | 0.257 | 0.246 | 0.245 | 0.278 | 0.320 | 0.266 |
| 0.277 | 0.313 | 0.319 | 0.251 | 0.251 | 0.257 | 0.314 | 0.258 | 0.243 |
| 0.287 | 0.336 | 0.372 | 0.269 | 0.247 | 0.249 | 0.288 | 0.325 | 0.298 |
| 0.344 | 0.306 | 0.306 | 0.251 | 0.249 | 0.254 | 0.266 | 0.297 | 0.279 |
| 0.315 | 0.323 | 0.317 | 0.254 | 0.253 | 0.243 | 0.271 | 0.269 | 0.259 |
| 0.346 | 0.324 | 0.321 | 0.249 | 0.252 | 0.245 | 0.281 | 0.261 | 0.371 |
| 0.291 | 0.308 | 0.305 | 0.244 | 0.242 | 0.241 | 0.275 | 0.255 | 0.274 |
| 0.264 | 0.291 | 0.288 | 0.259 | 0.254 | 0.254 | 0.260 | 0.268 | 0.251 |
| 0.292 | 0.334 | 0.271 | 0.253 | 0.251 | 0.245 | 0.266 | 0.261 | 0.319 |
| 0.313 | 0.278 | 0.331 | 0.247 | 0.257 | 0.246 | 0.272 | 0.282 | 0.255 |
| 0.319 | 0.298 | 0.314 | 0.245 | 0.253 | 0.259 | 0.296 | 0.261 | 0.252 |
| 0.295 | 0.340 | 0.290 | 0.257 | 0.253 | 0.248 | 0.322 | 0.266 | 0.247 |
| 0.349 | 0.313 | 0.312 | 0.247 | 0.258 | 0.245 | 0.284 | 0.258 | 0.249 |
| 0.344 | 0.348 | 0.340 | 0.240 | 0.268 | 0.248 | 0.272 | 0.279 | 0.311 |
| 0.316 | 0.315 | 0.326 | 0.237 | 0.253 | 0.252 | 0.321 | 0.310 | 0.252 |
| 0.350 | 0.315 | 0.293 | 0.243 | 0.244 | 0.233 | 0.246 | 0.281 | 0.268 |
| 0.328 | 0.299 | 0.316 | 0.251 | 0.234 | 0.254 | 0.264 | 0.256 | 0.287 |
| 0.311 | 0.329 | NA | 0.240 | 0.253 | NA | 0.269 | 0.277 | NA |

A BIER vessel was set at 121° C. and 10 test units were run in each of the following cycles for each of the three lots packaged manually: 5, 7, 8, 9, 10, 11, 12, 13 and 15 minutes with 90 units tested for each lot. Analysis was performed as described in Example 1. The number of positives over number tested was recorded with a read-out time of 20 seconds.

TABLE 12

BIER Vessel Tests

| Exposure Time | Lot A | | Lot B | | Lot C | |
|---|---|---|---|---|---|---|
| | manual | auto | manual | auto | manual | auto |
| 5 minutes | 10/10 | 10/10 | 10/10 | 10/10 | 10/10 | 10/10 |
| 7 minutes | 10/10 | 10/10 | 10/10 | 10/10 | 10/10 | 10/10 |
| 8 minutes | 10/10 | 10/10 | 10/10 | 10/10 | 10/10 | 10/10 |
| 9 minutes | 5/10 | 9/10 | 8/10 | 10/10 | 7/10 | 6/10 |
| 10 minutes | 3/10 | 5/10 | 6/10 | 10/10 | 5/10 | 4/10 |
| 11 minutes | 3/10 | 4/10 | 2/10 | 10/10 | 2/10 | 3/10 |
| 12 minutes | 0/10 | 2/10 | 0/10 | 3/10 | 1/10 | 2/10 |
| 13 minutes | 0/10 | 0/10 | 1/10 | 3/10 | 0/10 | 0/10 |
| 15 minutes | 0/10 | 0/10 | 0/10 | 0/10 | 0/10 | 0/10 |

Overall, the enzymatic activity of the tablets decreased as the time of exposure increased. Five minute exposure in an autoclave showed 100% positive (30/30) and the 15 minute exposure showed 100% negative (0/30).

Automated assembly of test units does not adversely affect performance of the test unit (i.e., 100% positive for a 5 minute exposure to steam in a BIER vessel and 100% negative for a 15 minute exposure to steam in a BIER vessel). Performance of the automated test unit does not significantly differ from the performance of the test unit manufactured manually, showing that the automated foam stuffer is acceptable for use.

Five test units prepared by manually inserting foam and the same number from automatically packaged lots A, B and C were placed in a conventional 121° C. gravity autoclave. The autoclave was run for a 5 minute cycle. Analysis was performed according to Example 1. All indicators tested positive.

Five test units from each of the above lots were placed in a conventional 121° C. gravity autoclave. The autoclave was run for a 15 minute cycle. Analysis was performed as above. All indicators tested negative.

Example 10

Rapid Sterility Indicator with a Closed-Cell Foam in a Plasma-Phase Hydrogen Peroxide Sterilizer The rapid sterility indicator as described in Example 5 was used with some modifications, the preferred foam length was changed from 0.375 inches to 1.0 inches, diameter is approximately 0.5". The preferred foam type was changed to a polyethylene closed-cell foam, referred to as Fireflex or Melamine. The density of the foam as approximately 0.7 lbs/cubic foot, elongation=10%, compression at 50%=6.2%, compression at 75%=8.5%, compression at 90%=14.4%, and heat resistant to 302° F. Rapid sterility indicators were exposed to survival and kill cycles in the plasma-phase hydrogen peroxide sterilizer. Survival cycles are cycles with short sterilant diffusion times in which indicators should test positive, indicating proper sterilization conditions were not met. Kill cycles are the standard cycles times in which the indicator should test negative indicating proper sterilization conditions were met.

The survival time for the plasma-phase hydrogen peroxide sterilizer was determined to be a 6.5 minute diffusion time. Plasma time was held constant at 15 minutes and vaporizer time was 0.5 minutes. Kill time was determined to be a 35 minute diffusion time. Rapid sterility indicator test units were placed into the sterilizer and exposed to the survival and kill cycles and processed as in Example 1. Results were recorded 20 seconds after adding the indicator solution to the test unit.

TABLE 13

Plasma-phase $H_2O_2$ Sterilizer-Survival/Kill Times

| Foam Length | Survival[1] | Kill[2] |
|---|---|---|
| 1.0" | 10/10 | 0/10 |

1=Diffusion time 6.5 minutes; Plasma time 15 minutes; Vaporizer time 0.5 minutes; and Readout time 20 seconds
2=Diffusion time 35 minutes; Plasma time 15 minutes; Vaporizer time 0.5 minutes; and Readout time 20 seconds In the tests shown in Table 13, the rapid sterility indicator showed the proper survival/kill performance in a STERRAD sterilizer. By adjusting the foam length or the type of foam, the desired survival/kill times could be met. This demonstrates that the rapid sterility indicator can be used to test the effectiveness of the STERRAD hydrogen peroxide sterilizer. The foam length of 1.0 inches provided the proper survival/kill results at 20 seconds after addition of the enzyme system reagents.

These tests demonstrate that the rapid sterility indicator is effective for monitoring the plasma-phase hydrogen peroxide sterilizer. All positives were observed after the survival time and all negatives were observed after the kill time. The RSI challenge pack can also be modified to work in this sterilizer.

Example 11

A Single Container Reusable Pack Challenge Packs with Unique High Resistant Parameters The challenge pack described in example 7 can be modified to create an extremely resistant challenge. By increasing the foam density and/or making the steam entry holes smaller, the challenge pack will enable the indicator inside the pack to survive very long exposures to sterilization. A reusable challenge pack can be created from one container with a closure device, one piece of foam and a sterility indicator. A reusable challenge pack is made of material that can withstand multiple exposures to sterilization and can be easily opened and closed. The container is made from plastic or glass, preferably plastic. The container is approximately 1½" diameter, 2½" long with a screw cap. The two steam entry holes are approximately ⅛" in diameter and the holes are located approximately ¼" below the cap. A tubular piece of open cell, 4–6 pound polyurethane foam approximately 1½" long, 1½" outer diameter (inner diameter ⅜") is placed into the container. The rapid sterility indicator test unit as described in Example 1 is placed into the foam insert. The foam fits tightly into the container and the test unit fits tightly into the foam. The cap of the container is screwed into place and creates a tight seal so that the only pathway for steam to enter the challenge pack is through the small openings, passing through the foam to reach the indicator. The pack may also contain a heat sink material such as a metal object.

These challenge packs were placed into a steam sterilizer operating at 134° C. (pre-vac sterilizer) and exposed to the predetermined survival and kill cycles. For this high resistant challenge pack the survival cycle included exposure to 4 pre-vacuum cycles of temperature range of 60–130° C. for 8 minutes, then 1 minute of exposure to 134° C. The kill cycle included exposure to the 4 pre-vacuum cycles and a 4 minute exposure to 134° C. After the kill cycle indicators should test negative indicating proper sterilization conditions were met and the indicators should be positive after the survival cycles. After the cycles were complete, the container was opened and the indicator retrieved. The rapid sterility indicators were processed as described in Example 1, the results are obtained at 20 seconds or less after adding the indicator solution.

TABLE 14

One Container Reusable High Resistant Challenge Pack

| | 134° C. Pre-Vacuum Steam Sterilizer (Total steam exposure time, the first 8 minutes temperature is 60–130° C.) | |
|---|---|---|
| | Survival time 9 min. | Kill time 12 min. |
| Rapid Sterility Indicator in one container reusable challenge pack | 10/10 | 0/10 |

The results in Table 12 are recorded as the number positive over the number tested. As shown, when exposed to an extremely long survival cycle, including high temperatures, all indicators within the high resistant challenge pack tested positive. When exposed to the kill cycle time, all indicators tested negative. This table shows that the challenge pack design provides acceptable results. This resistant challenge pack has the unique feature of surviving very long cycles. It is actually testing the over-kill parameters built into the sterilizer. This also allows the user to do a validation in the standardized hospital cycles. The user can expose the indicator to the 3–4 pre-vacuums in a conventional autoclave and observe positive results. In the past, positive results of sterility indicators were only seen in BIER vessels or special research and development sterilizers that were able to perform one quick vacuum rather than the 3–4 long vacuums. This challenge pack also has the unique feature such that the user can reassemble the pack by placing a new indicator into the container, closing the container, and using it for another test.

Other embodiments and uses of the invention will be apparent to those skilled in the art from consideration of the specification and practice of the invention disclosed herein. All U.S. patents and other documents referenced herein, for whatever reason, are specifically incorporated by reference. It is intended that the specification and examples be considered exemplary only, with the true scope and spirit of the invention being indicated by the following claims.

We claim:

1. A test indicator for determining the effectiveness of a sterilization procedure comprising:

a container having liquid impermeable and substantially gas non-absorptive walls and at least one opening communicating with an interior chamber, the chamber containing biological material used as an indicator of destruction of living organisms by the sterilization procedure, a gas-transmissive plug positioned in the at least one opening such that movement of gas between the environment surrounding the test indicator and the interior chamber occurs through the gas-transmissive plug.

2. The test indicator of claim 1 wherein the gas-transmissive plug is compressible and has an inside portion inside said at least one opening and an overhang portion extending outside of said at least one opening.

3. The test indicator of claim 1 wherein the overhang portion is less than or equal to about 0.5 inches.

4. The test indicator of claim 1 wherein the at least one opening has a cross-sectional area of from about 0.03 to about 0.20 square inches.

5. The test indicator of claim 1 wherein the gas-transmissive plug has a non-compressed cross-sectional area of from about 0.2 to about 3.5 square inches, an inside portion of from about 0.4 to about 1.2 inches.

6. The test indicator of claim 1 wherein the sterilization procedure comprises steam heat, chemical sterilant, plasma, dry heat or a combination thereof.

7. The test indicator of claim 1 wherein the biological material comprises microorganisms, bacterial spores, enzymes, at least one component of an interactive enzyme system or a combination thereof.

8. The test indicator of claim 7 wherein the biological material comprises a granulation product.

9. The test indicator of claim 7 wherein the interactive enzyme system comprises a granulation product of glucose dehydrogenase and diaphorase.

10. A sterility indicator for determining the effectiveness of a sterilization procedure comprising:

a container having liquid impermeable and substantially gas non-absorptive walls and at least one opening communicating with an interior chamber, the chamber containing biological material used as an indicator of destruction of living organisms by the sterilization procedure;

a gas-transmissive insert adjustably positioned in the at least one opening such that movement of gas between the environment surrounding the sterility indicator and the interior chamber occurs through the gas-transmissive insert.

11. The sterility indicator of claim 10 wherein the gas transmissive insert is between about 0.75 to 1.5 inches in length and extends from about 0.1 to about 0.5 inches outward from said at least one opening.

12. A method for adjusting sensitivity of the sterility indicator of claim 10 to a predetermined environmental parameter comprising the steps of:
   a) exposing a test indicator substantially identical to the sterility indicator to the sterilization procedure;
   b) determining the effectiveness of the test indicator for reacting to the predetermined environmental parameter;
   c) adjusting the position or composition of the gas-transmissive insert of another test indicator;
   d) exposing said another test indicator to the sterilization process and determining the effectiveness of the another test indicator for reacting to the predetermined environmental parameter and from the effectiveness determined for each test indicator;
   e) adjusting the sensitivity of said sterility indicator.

13. The method of claim 12 wherein the sterilization procedure comprises exposing the test indicator to steam at 121° C., 132° C. or 134° C.

14. The method of claim 12 wherein the sterilization procedure comprises exposing the test indicator to a sterilant.

15. The method of claim 14 wherein the sterilant is ethylene oxide or plasma-phase hydrogen peroxide.

16. The method of claim 12 wherein the predetermined environmental parameter is selected from the group consisting of temperature, time, pressure, humidity, concentration of sterilant, penetration of sterilant, air removal or a combination thereof.

17. The method of claim 12 wherein the gas-transmissive insert comprises an overhang portion and the position of said insert is adjusted by extending or retracting an overhang portion that extends outwardly beyond said at least one opening.

18. The method of claim 17 wherein the overhang portion of the gas-transmissive insert is extended to increase sensitivity of the indicator to a combination of increased temperature, humidity and pressure.

19. The method of claim 12 wherein the gas-transmissive insert is composed of a compressible material and the composition of said insert is adjusted by increasing or decreasing the density of said compressible material.

20. The method of claim 19 wherein the density of the compressible material is decreased to increase sensitivity of the indicator to a combination of increased temperature, humidity and pressure or the presence of chemical sterilants.

21. A test pack for detecting a predetermined environmental parameter of a sterilization process comprising:
   a container having liquid impermeable and substantially gas non-absorptive walls and at least one opening communicating with an interior chamber, said chamber containing;
   a test indicator comprising another container having liquid impermeable and substantially gas non-absorptive walls and at least one opening communicating with an interior chamber;
   wherein gas-transmissive inserts are positioned over each of said openings and said environmental parameter can move from the exterior of said test pack to said interior chamber of said test pack and to said interior chamber of said test indicator.

22. The test pack of claim 21 wherein the environmental parameter is the presence of a vacuum, the concentration of a sterilant, pressure, penetration of sterilant, radiation or an amount of heat.

23. The test pack of claim 21 wherein the gas-transmissive inserts comprise foam that conform to the inside dimension of said containers.

24. The test pack of claim 21 which can be reused upon substitution of said test indicator.

25. The test pack of claim 21 wherein the gas-transmissive insert is a foam cylinder with an outer diameter of about 1 to about 2 inches, an inner diameter of about 1¼ inches, and a height of about 1 to about 3 inches.

26. The test pack of claim 21 wherein the container is about 1 to about 4 inches in height and about 1 to about 3 inches in diameter, has a removable cap, and contains one or more holes of about ⅛ to ½ inches in diameter in said container.

* * * * *